(12) United States Patent
Baril et al.

(10) Patent No.: US 11,259,887 B2
(45) Date of Patent: Mar. 1, 2022

(54) FEEDBACK MECHANISMS FOR HANDLE ASSEMBLIES

(71) Applicant: Covidien LP, Mansfield, MA (US)

(72) Inventors: Jacob C. Baril, Norwalk, CT (US); Christopher M. Meehan, New Haven, CT (US); Brian J. Creston, West Haven, CT (US); Ernest A. Addi, Middletown, CT (US); Matthew Malavenda, West Haven, CT (US); Thomas A. Zammataro, Hamden, CT (US); Amy Kung, Milford, CT (US)

(73) Assignee: Covidien LP, Mansfield, MA (US)

( * ) Notice: Subject to any disclaimer, the term of this patent is extended or adjusted under 35 U.S.C. 154(b) by 257 days.

(21) Appl. No.: 16/419,123

(22) Filed: May 22, 2019

(65) Prior Publication Data

US 2020/0046443 A1    Feb. 13, 2020

Related U.S. Application Data

(60) Provisional application No. 62/717,023, filed on Aug. 10, 2018.

(51) Int. Cl.
*A61B 34/00* (2016.01)
*A61B 17/00* (2006.01)
*A61B 17/04* (2006.01)

(52) U.S. Cl.
CPC .............. *A61B 34/76* (2016.02); *A61B 17/00* (2013.01); *A61B 17/0487* (2013.01); *A61B 17/00234* (2013.01); *A61B 2017/0042* (2013.01); *A61B 2017/0046* (2013.01); *A61B 2017/00115* (2013.01); *A61B 2017/0488* (2013.01)

(58) Field of Classification Search
CPC ..... A61B 17/29; A61B 17/072; A61B 17/128; A61B 34/00; A61B 17/00; A61B 17/0487; A61B 17/1285; A61B 34/76; A61B 2017/00115; A61B 2017/00128; A61B 17/00234; A61B 2017/0042;
(Continued)

(56) References Cited

U.S. PATENT DOCUMENTS 3,120,230 A    2/1964  Skold
3,638,847 A    2/1972  Noiles et al.
(Continued)

FOREIGN PATENT DOCUMENTS

CN    103251441 A    8/2013
EP    0732078 A2     9/1996
(Continued)

OTHER PUBLICATIONS

European Search Report dated Dec. 12, 2019, issued in EP Appln. No. 19191076, nine pages.
(Continued)

*Primary Examiner* — George J Ulsh
(74) *Attorney, Agent, or Firm* — Carter, DeLuca & Farrell LLP

(57) ABSTRACT

A handle assembly for actuating an end effector includes a feedback mechanism for providing an audible and/or tactical response to indicate to the user that the handle assembly is fully actuated. The feedback mechanism may include a hammer member configured to strike a surface of the handle assembly to create the audible and/or tactical response.

20 Claims, 17 Drawing Sheets

(58) Field of Classification Search
CPC .... A61B 2017/0046; A61B 2017/0488; A61B 2017/2919; A61B 2090/0811
See application file for complete search history.

(56) References Cited

U.S. PATENT DOCUMENTS

| | | |
|---|---|---|
| 4,226,242 A | 10/1980 | Jarvik |
| 4,242,902 A | 1/1981 | Green |
| 4,296,751 A | 10/1981 | Blake, III et al. |
| 4,372,316 A | 2/1983 | Blake, III et al. |
| 4,408,603 A | 10/1983 | Blake, III et al. |
| 4,480,640 A | 11/1984 | Becht |
| 4,480,641 A | 11/1984 | Failla et al. |
| 4,487,204 A | 12/1984 | Hrouda |
| 4,487,205 A | 12/1984 | Di Giovanni et al. |
| 4,491,133 A | 1/1985 | Menges et al. |
| 4,492,232 A | 1/1985 | Green |
| 4,498,476 A | 2/1985 | Cerwin et al. |
| 4,500,024 A | 2/1985 | DiGiovanni et al. |
| 4,509,518 A | 4/1985 | McGarry et al. |
| 4,512,345 A | 4/1985 | Green |
| 4,522,207 A | 6/1985 | Klieman et al. |
| 4,532,925 A | 8/1985 | Blake, III |
| 4,534,351 A | 8/1985 | Rothfuss et al. |
| 4,545,377 A | 10/1985 | Cerwin et al. |
| 4,549,544 A | 10/1985 | Favaron |
| 4,556,058 A | 12/1985 | Green |
| 4,557,263 A | 12/1985 | Green |
| 4,562,839 A | 1/1986 | Blake, III et al. |
| 4,572,183 A | 2/1986 | Juska |
| 4,576,165 A | 3/1986 | Green et al. |
| 4,576,166 A | 3/1986 | Montgomery et al. |
| 4,590,937 A | 5/1986 | Deniega |
| 4,598,711 A | 7/1986 | Deniega |
| 4,602,631 A | 7/1986 | Funatsu |
| 4,611,595 A | 9/1986 | Klieman et al. |
| 4,612,932 A | 9/1986 | Caspar et al. |
| 4,616,650 A | 10/1986 | Green et al. |
| 4,616,651 A | 10/1986 | Golden |
| 4,624,254 A | 11/1986 | McGarry et al. |
| 4,637,395 A | 1/1987 | Caspar et al. |
| 4,646,740 A | 3/1987 | Peters et al. |
| 4,647,504 A | 3/1987 | Kimimura et al. |
| 4,658,822 A | 4/1987 | Kees, Jr. |
| 4,660,558 A | 4/1987 | Kees, Jr. |
| 4,662,373 A | 5/1987 | Montgomery et al. |
| 4,662,374 A | 5/1987 | Blake, III |
| 4,671,278 A | 6/1987 | Chin |
| 4,671,282 A | 6/1987 | Tretbar |
| 4,674,504 A | 6/1987 | Klieman et al. |
| 4,681,107 A | 7/1987 | Kees, Jr. |
| 4,696,396 A | 9/1987 | Samuels |
| 4,702,247 A | 10/1987 | Blake, III et al. |
| 4,706,668 A | 11/1987 | Backer |
| 4,712,549 A | 12/1987 | Peters et al. |
| 4,726,372 A | 2/1988 | Perlin |
| 4,733,664 A | 3/1988 | Kirsch et al. |
| 4,733,666 A | 3/1988 | Mercer, Jr. |
| 4,759,364 A | 7/1988 | Boebel |
| 4,765,335 A | 8/1988 | Schmidt et al. |
| 4,777,949 A | 10/1988 | Perlin |
| 4,777,950 A | 10/1988 | Kees, Jr. |
| 4,796,625 A | 1/1989 | Kees, Jr. |
| 4,799,481 A | 1/1989 | Transue et al. |
| 4,815,466 A | 3/1989 | Perlin |
| 4,817,604 A | 4/1989 | Smith, III |
| 4,821,721 A | 4/1989 | Chin et al. |
| 4,822,348 A | 4/1989 | Casey |
| 4,827,930 A | 5/1989 | Kees, Jr. |
| 4,834,096 A | 5/1989 | Oh et al. |
| 4,850,355 A | 7/1989 | Brooks et al. |
| 4,854,317 A | 8/1989 | Braun |
| 4,856,517 A | 8/1989 | Collins et al. |
| 4,929,239 A | 5/1990 | Braun |
| 4,929,240 A | 5/1990 | Kirsch et al. |
| 4,931,058 A | 6/1990 | Cooper |
| 4,932,955 A | 6/1990 | Merz et al. |
| 4,934,364 A | 6/1990 | Green |
| 4,943,298 A | 7/1990 | Fujita et al. |
| 4,957,500 A | 9/1990 | Liang et al. |
| 4,966,603 A | 10/1990 | Focelle et al. |
| 4,967,949 A | 11/1990 | Sandhaus |
| 4,983,176 A | 1/1991 | Cushman et al. |
| 4,988,355 A | 1/1991 | Leveen et al. |
| 5,002,552 A | 3/1991 | Casey |
| 5,026,379 A | 6/1991 | Yoon |
| 5,030,224 A | 7/1991 | Wright et al. |
| 5,030,226 A | 7/1991 | Green et al. |
| 5,032,127 A | 7/1991 | Frazee et al. |
| 5,035,692 A | 7/1991 | Lyon et al. |
| 5,047,038 A | 9/1991 | Peters et al. |
| 5,049,152 A | 9/1991 | Simon et al. |
| 5,049,153 A | 9/1991 | Nakao et al. |
| 5,053,045 A | 10/1991 | Schmidt et al. |
| 5,059,202 A | 10/1991 | Liang et al. |
| 5,062,846 A | 11/1991 | Oh et al. |
| 5,078,731 A | 1/1992 | Hayhurst |
| 5,084,057 A | 1/1992 | Green et al. |
| 5,100,416 A | 3/1992 | Oh et al. |
| 5,100,420 A | 3/1992 | Green et al. |
| 5,104,394 A | 4/1992 | Knoepfler |
| 5,104,395 A | 4/1992 | Thornton et al. |
| 5,112,343 A | 5/1992 | Thornton |
| 5,122,150 A | 6/1992 | Puig |
| 5,127,915 A | 7/1992 | Mattson |
| 5,129,885 A | 7/1992 | Green et al. |
| 5,156,608 A | 10/1992 | Troidl et al. |
| 5,160,339 A | 11/1992 | Chen et al. |
| 5,163,945 A | 11/1992 | Ortiz et al. |
| 5,171,247 A | 12/1992 | Hughett et al. |
| 5,171,249 A | 12/1992 | Stefanchik et al. |
| 5,171,250 A | 12/1992 | Yoon |
| 5,171,251 A | 12/1992 | Bregen et al. |
| 5,171,252 A | 12/1992 | Friedland |
| 5,171,253 A | 12/1992 | Klieman |
| 5,192,288 A | 3/1993 | Thompson et al. |
| 5,197,970 A | 3/1993 | Green et al. |
| 5,199,566 A | 4/1993 | Ortiz et al. |
| 5,201,746 A | 4/1993 | Shichman |
| 5,201,900 A | 4/1993 | Nardella |
| 5,207,691 A | 5/1993 | Nardella |
| 5,207,692 A | 5/1993 | Kraus et al. |
| 5,217,473 A | 6/1993 | Yoon |
| 5,219,353 A | 6/1993 | Garvey, III et al. |
| 5,246,450 A | 9/1993 | Thornton et al. |
| 5,269,792 A | 12/1993 | Kovac et al. |
| 5,281,228 A | 1/1994 | Wolfson |
| 5,282,807 A | 2/1994 | Knoepfler |
| 5,282,808 A | 2/1994 | Kovac et al. |
| 5,282,832 A | 2/1994 | Toso et al. |
| 5,289,963 A | 3/1994 | McGarry et al. |
| 5,290,299 A | 3/1994 | Fain et al. |
| 5,300,081 A | 4/1994 | Young et al. |
| 5,304,183 A | 4/1994 | Gourlay et al. |
| 5,306,280 A | 4/1994 | Bregen et al. |
| 5,306,283 A | 4/1994 | Conners |
| 5,312,426 A | 5/1994 | Segawa et al. |
| 5,330,442 A | 7/1994 | Green et al. |
| 5,330,487 A | 7/1994 | Thornton et al. |
| 5,336,458 A | 8/1994 | Hutchison et al. |
| 5,340,360 A | 8/1994 | Stefanchik |
| 5,342,373 A | 8/1994 | Stefanchik et al. |
| 5,354,304 A | 10/1994 | Mien et al. |
| 5,354,306 A | 10/1994 | Garvey, III et al. |
| 5,359,993 A | 11/1994 | Slater et al. |
| 5,366,458 A | 11/1994 | Korthoff et al. |
| 5,366,459 A | 11/1994 | Yoon |
| 5,368,600 A | 11/1994 | Failla et al. |
| 5,382,253 A | 1/1995 | Hogendijk |
| 5,382,254 A | 1/1995 | McGarry et al. |
| 5,382,255 A | 1/1995 | Castro et al. |
| 5,383,881 A | 1/1995 | Green et al. |
| 5,395,375 A | 3/1995 | Turkel et al. |
| 5,395,381 A | 3/1995 | Green et al. |

(56) References Cited

U.S. PATENT DOCUMENTS

| | | |
|---|---|---|
| 5,403,327 A | 4/1995 | Thornton et al. |
| 5,409,498 A | 4/1995 | Braddock et al. |
| 5,413,584 A | 5/1995 | Schulze |
| 5,423,835 A | 6/1995 | Green et al. |
| 5,425,740 A | 6/1995 | Hutchinson, Jr. |
| 5,431,667 A | 7/1995 | Thompson et al. |
| 5,431,668 A | 7/1995 | Burbank, III et al. |
| 5,431,669 A | 7/1995 | Thompson et al. |
| 5,439,468 A | 8/1995 | Schulze et al. |
| 5,441,509 A | 8/1995 | Vidal et al. |
| 5,447,513 A | 9/1995 | Davison et al. |
| 5,448,042 A | 9/1995 | Robinson et al. |
| 5,449,365 A | 9/1995 | Green et al. |
| 5,462,555 A | 10/1995 | Bolanos et al. |
| 5,462,558 A | 10/1995 | Kolesa et al. |
| 5,464,416 A | 11/1995 | Steckel |
| 5,474,566 A | 12/1995 | Alesi et al. |
| 5,474,567 A | 12/1995 | Stefanchik et al. |
| 5,474,572 A | 12/1995 | Hayhurst |
| 5,487,746 A | 1/1996 | Yu et al. |
| 5,501,693 A | 3/1996 | Gravener |
| 5,509,920 A | 4/1996 | Phillips et al. |
| 5,514,149 A | 5/1996 | Green et al. |
| 5,520,701 A | 5/1996 | Lerch |
| 5,522,823 A | 6/1996 | Kuntz et al. |
| 5,527,318 A | 6/1996 | McGarry |
| 5,527,319 A | 6/1996 | Green et al. |
| 5,527,320 A | 6/1996 | Carruthers et al. |
| 5,542,949 A | 8/1996 | Yoon |
| 5,547,474 A | 8/1996 | Kloeckl et al. |
| 5,562,655 A | 10/1996 | Mittelstadt et al. |
| 5,569,274 A | 10/1996 | Rapacki et al. |
| 5,571,121 A | 11/1996 | Heifetz |
| 5,575,802 A | 11/1996 | McQuilkin et al. |
| 5,582,615 A | 12/1996 | Foshee et al. |
| 5,584,840 A | 12/1996 | Ramsey et al. |
| 5,591,178 A | 1/1997 | Green et al. |
| 5,593,414 A | 1/1997 | Shipp et al. |
| 5,593,421 A | 1/1997 | Bauer |
| 5,601,573 A | 2/1997 | Berg et al. |
| 5,601,574 A | 2/1997 | Stefanchik et al. |
| 5,607,436 A | 3/1997 | Pratt et al. |
| 5,618,291 A | 4/1997 | Thompson et al. |
| 5,618,306 A | 4/1997 | Roth et al. |
| 5,620,452 A | 4/1997 | Yoon |
| 5,626,585 A | 5/1997 | Mittelstadt et al. |
| 5,626,586 A | 5/1997 | Pistl et al. |
| 5,626,592 A | 5/1997 | Phillips et al. |
| RE35,525 E | 6/1997 | Stefanchik et al. |
| 5,634,930 A | 6/1997 | Thornton et al. |
| 5,643,291 A | 7/1997 | Pier et al. |
| 5,645,551 A | 7/1997 | Green et al. |
| 5,645,553 A | 7/1997 | Kolesa et al. |
| 5,649,937 A | 7/1997 | Bito et al. |
| 5,653,720 A | 8/1997 | Johnson et al. |
| 5,662,676 A | 9/1997 | Koninckx |
| 5,662,679 A | 9/1997 | Voss et al. |
| 5,665,097 A | 9/1997 | Baker et al. |
| 5,676,676 A | 10/1997 | Porter |
| 5,681,330 A | 10/1997 | Hughett et al. |
| 5,683,405 A | 11/1997 | Yacoubian et al. |
| 5,695,502 A | 12/1997 | Pier et al. |
| 5,695,505 A | 12/1997 | Yoon |
| 5,697,938 A | 12/1997 | Jensen et al. |
| 5,700,270 A | 12/1997 | Peyser et al. |
| 5,700,271 A | 12/1997 | Whitfield et al. |
| 5,702,048 A | 12/1997 | Eberlin |
| 5,709,706 A | 1/1998 | Kienzle et al. |
| 5,713,911 A | 2/1998 | Racenet et al. |
| 5,713,912 A | 2/1998 | Porter |
| 5,720,756 A | 2/1998 | Green et al. |
| 5,722,982 A | 3/1998 | Ferreira et al. |
| 5,725,537 A | 3/1998 | Green et al. |
| 5,725,538 A | 3/1998 | Green et al. |
| 5,725,542 A | 3/1998 | Yoon |
| 5,733,295 A | 3/1998 | Back et al. |
| 5,743,310 A | 4/1998 | Moran |
| 5,755,726 A | 5/1998 | Pratt et al. |
| 5,766,189 A | 6/1998 | Matsuno |
| 5,769,857 A | 6/1998 | Reztzov et al. |
| 5,772,673 A | 6/1998 | Cuny et al. |
| 5,776,146 A | 7/1998 | Sackier et al. |
| 5,776,147 A | 7/1998 | Dolendo |
| 5,779,718 A | 7/1998 | Green et al. |
| 5,779,720 A | 7/1998 | Walder-Utz et al. |
| 5,782,844 A | 7/1998 | Yoon et al. |
| 5,788,698 A | 8/1998 | Savornin |
| 5,792,149 A | 8/1998 | Sherts et al. |
| 5,792,150 A | 8/1998 | Pratt et al. |
| 5,797,922 A | 8/1998 | Hessel et al. |
| 5,810,853 A | 9/1998 | Yoon |
| 5,817,116 A | 10/1998 | Takahashi et al. |
| 5,824,547 A | 10/1998 | Hashino et al. |
| 5,824,548 A | 10/1998 | Hearn |
| 5,827,306 A | 10/1998 | Yoon |
| 5,833,695 A | 11/1998 | Yoon |
| 5,833,696 A | 11/1998 | Whitfield et al. |
| 5,833,700 A | 11/1998 | Fogelberg et al. |
| 5,835,199 A | 11/1998 | Phillips et al. |
| 5,843,097 A | 12/1998 | Mayenberger et al. |
| 5,843,101 A | 12/1998 | Fry |
| 5,846,255 A | 12/1998 | Casey |
| 5,849,019 A | 12/1998 | Yoon |
| 5,858,018 A | 1/1999 | Shipp et al. |
| 5,861,005 A | 1/1999 | Kontos |
| 5,868,759 A | 2/1999 | Peyser et al. |
| 5,868,761 A | 2/1999 | Nicholas et al. |
| 5,876,410 A | 3/1999 | Petillo |
| 5,895,394 A | 4/1999 | Kienzle et al. |
| 5,897,565 A | 4/1999 | Foster |
| 5,904,693 A | 5/1999 | Dicesare et al. |
| 5,913,862 A | 6/1999 | Ramsey et al. |
| 5,918,791 A | 7/1999 | Sorrentino et al. |
| 5,921,991 A | 7/1999 | Whitehead et al. |
| 5,921,996 A | 7/1999 | Sherman |
| 5,921,997 A | 7/1999 | Fogelberg et al. |
| 5,928,251 A | 7/1999 | Aranyi et al. |
| 5,938,667 A | 8/1999 | Peyser et al. |
| 5,951,574 A | 9/1999 | Stefanchik et al. |
| 5,972,003 A | 10/1999 | Rousseau et al. |
| 5,976,159 A | 11/1999 | Bolduc et al. |
| 5,993,465 A | 11/1999 | Shipp et al. |
| 6,004,335 A | 12/1999 | Vaitekunas et al. |
| 6,017,358 A | 1/2000 | Yoon et al. |
| 6,044,971 A | 4/2000 | Esposito et al. |
| RE36,720 E | 5/2000 | Green et al. |
| 6,059,799 A | 5/2000 | Aranyi et al. |
| 6,099,536 A | 8/2000 | Petillo |
| 6,099,537 A | 8/2000 | Sugai et al. |
| 6,139,555 A | 10/2000 | Hart et al. |
| 6,210,418 B1 | 4/2001 | Storz et al. |
| 6,217,590 B1 | 4/2001 | Levinson |
| 6,228,097 B1 | 5/2001 | Levinson et al. |
| 6,241,740 B1 | 6/2001 | Davis et al. |
| 6,258,105 B1 | 7/2001 | Hart et al. |
| 6,261,302 B1 | 7/2001 | Voegele et al. |
| 6,273,898 B1 | 8/2001 | Kienzle et al. |
| 6,277,131 B1 | 8/2001 | Kalikow |
| 6,306,149 B1 | 10/2001 | Meade |
| 6,318,619 B1 | 11/2001 | Lee |
| 6,322,571 B1 | 11/2001 | Adams |
| 6,350,269 B1 | 2/2002 | Shipp et al. |
| 6,352,541 B1 | 3/2002 | Kienzle et al. |
| 6,391,035 B1 | 5/2002 | Appleby et al. |
| 6,423,079 B1 | 7/2002 | Blake, III |
| 6,428,548 B1 | 8/2002 | Durgin et al. |
| 6,440,144 B1 | 8/2002 | Bacher |
| 6,461,363 B1 | 10/2002 | Gadberry et al. |
| 6,464,710 B1 | 10/2002 | Foster |
| 6,494,886 B1 | 12/2002 | Wilk et al. |
| 6,517,536 B2 | 2/2003 | Hooven et al. |
| 6,520,972 B2 | 2/2003 | Peters |
| 6,527,786 B1 | 3/2003 | Davis et al. |
| 6,537,289 B1 | 3/2003 | Kayan et al. |

(56) References Cited

U.S. PATENT DOCUMENTS

| | | |
|---|---|---|
| 6,546,935 B2 | 4/2003 | Hooven |
| 6,551,333 B2 | 4/2003 | Kuhns et al. |
| 6,569,171 B2 | 5/2003 | DeGuillebon et al. |
| 6,579,304 B1 | 6/2003 | Hart et al. |
| 6,599,298 B1 | 7/2003 | Forster et al. |
| 6,602,252 B2 | 8/2003 | Mollenauer |
| 6,607,540 B1 | 8/2003 | Shipp |
| 6,613,060 B2 | 9/2003 | Adams et al. |
| 6,626,916 B1 | 9/2003 | Yeung et al. |
| 6,626,922 B1 | 9/2003 | Hart et al. |
| 6,648,898 B1 | 11/2003 | Baxter |
| 6,652,538 B2 | 11/2003 | Kayan et al. |
| 6,652,539 B2 | 11/2003 | Shipp et al. |
| 6,673,083 B1 | 1/2004 | Kayan et al. |
| 6,676,659 B2 | 1/2004 | Hutchins et al. |
| 6,679,894 B2 | 1/2004 | Damarati |
| RE38,445 E | 2/2004 | Pistl et al. |
| 6,695,854 B1 | 2/2004 | Kayan et al. |
| 6,706,057 B1 | 3/2004 | Bidoia et al. |
| 6,716,226 B2 | 4/2004 | Sixto, Jr. et al. |
| 6,723,109 B2 | 4/2004 | Solingen |
| 6,743,240 B2 | 6/2004 | Smith et al. |
| 6,773,438 B1 | 8/2004 | Knodel et al. |
| 6,773,440 B2 | 8/2004 | Gannoe et al. |
| 6,776,783 B1 | 8/2004 | Frantzen et al. |
| 6,776,784 B2 | 8/2004 | Ginn |
| 6,780,195 B2 | 8/2004 | Porat |
| 6,793,663 B2 | 9/2004 | Kneifel et al. |
| 6,793,664 B2 | 9/2004 | Mazzocchi et al. |
| 6,802,848 B2 | 10/2004 | Anderson et al. |
| 6,814,742 B2 | 11/2004 | Kimura et al. |
| 6,818,009 B2 | 11/2004 | Hart et al. |
| 6,821,273 B2 | 11/2004 | Mollenauer |
| 6,821,284 B2 | 11/2004 | Sturtz et al. |
| 6,824,547 B2 | 11/2004 | Wilson, Jr. et al. |
| 6,824,548 B2 | 11/2004 | Smith et al. |
| 6,835,199 B2 | 12/2004 | McGuckin, Jr. et al. |
| 6,835,200 B2 | 12/2004 | Laufer et al. |
| 6,837,893 B2 | 1/2005 | Miller |
| 6,837,894 B2 | 1/2005 | Pugsley, Jr. et al. |
| 6,837,895 B2 | 1/2005 | Mayenberger |
| 6,840,945 B2 | 1/2005 | Manetakis et al. |
| 6,843,794 B2 | 1/2005 | Sixto, Jr. et al. |
| 6,849,078 B2 | 2/2005 | Durgin et al. |
| 6,849,079 B1 | 2/2005 | Blake, III et al. |
| 6,853,879 B2 | 2/2005 | Sunaoshi |
| 6,869,435 B2 | 3/2005 | Blake, III |
| 6,869,436 B2 | 3/2005 | Wendlandt |
| 6,889,116 B2 | 5/2005 | Jinno |
| 6,896,682 B1 | 5/2005 | McClellan et al. |
| 6,905,503 B2 | 6/2005 | Gifford, III et al. |
| 6,911,032 B2 | 6/2005 | Jugenheimer et al. |
| 6,911,033 B2 | 6/2005 | de Guillebon et al. |
| 6,913,607 B2 | 7/2005 | Ainsworth et al. |
| 6,916,327 B2 | 7/2005 | Northrup, III et al. |
| 6,923,818 B2 | 8/2005 | Muramatsu et al. |
| 6,939,356 B2 | 9/2005 | Debbas |
| 6,942,674 B2 | 9/2005 | Belef et al. |
| 6,942,676 B2 | 9/2005 | Buelna |
| 6,945,978 B1 | 9/2005 | Hyde |
| 6,945,979 B2 | 9/2005 | Kortenbach et al. |
| 6,949,107 B2 | 9/2005 | McGuckin, Jr. et al. |
| 6,953,465 B2 | 10/2005 | Dieck et al. |
| 6,955,643 B2 | 10/2005 | Gellman et al. |
| 6,959,852 B2 | 11/2005 | Shelton, IV et al. |
| 6,960,218 B2 | 11/2005 | Rennich |
| 6,960,221 B2 | 11/2005 | Ho et al. |
| 6,962,594 B1 | 11/2005 | Thevenet |
| 6,963,792 B1 | 11/2005 | Green |
| 6,964,363 B2 | 11/2005 | Wales et al. |
| 6,964,668 B2 | 11/2005 | Modesitt et al. |
| 6,966,875 B1 | 11/2005 | Longobardi |
| 6,966,917 B1 | 11/2005 | Suyker et al. |
| 6,966,919 B2 | 11/2005 | Sixto, Jr. et al. |
| 6,966,981 B2 | 11/2005 | Binder et al. |
| 6,969,391 B1 | 11/2005 | Gazzani |
| 6,972,023 B2 | 12/2005 | Whayne et al. |
| 6,972,027 B2 | 12/2005 | Fallin et al. |
| 6,973,770 B2 | 12/2005 | Schnipke et al. |
| 6,974,446 B2 | 12/2005 | Hommann et al. |
| 6,974,462 B2 | 12/2005 | Sater |
| 6,974,466 B2 | 12/2005 | Ahmed et al. |
| 6,974,475 B1 | 12/2005 | Wall |
| 6,981,505 B2 | 1/2006 | Krause et al. |
| 6,981,628 B2 | 1/2006 | Wales |
| 6,991,597 B2 | 1/2006 | Gellman et al. |
| 6,991,635 B2 | 1/2006 | Takamoto et al. |
| 7,052,504 B2 | 5/2006 | Hughett |
| 7,056,330 B2 | 6/2006 | Gayton |
| 7,108,703 B2 | 9/2006 | Danitz et al. |
| 7,144,402 B2 | 12/2006 | Kuester, III |
| 7,175,648 B2 | 2/2007 | Nakao |
| 7,179,265 B2 | 2/2007 | Manetakis et al. |
| 7,207,997 B2 | 4/2007 | Shipp et al. |
| 7,211,091 B2 | 5/2007 | Fowler et al. |
| 7,211,092 B2 | 5/2007 | Hughett |
| 7,214,230 B2 | 5/2007 | Brock et al. |
| 7,214,232 B2 | 5/2007 | Bowman et al. |
| 7,223,271 B2 | 5/2007 | Muramatsu et al. |
| 7,223,272 B2 | 5/2007 | Francese et al. |
| 7,232,445 B2 | 6/2007 | Kortenbach et al. |
| 7,261,724 B2 | 8/2007 | Molitor et al. |
| 7,261,725 B2 | 8/2007 | Binmoeller |
| 7,264,625 B1 | 9/2007 | Buncke |
| 7,288,098 B2 | 10/2007 | Huitema et al. |
| 7,297,149 B2 | 11/2007 | Vitali et al. |
| 7,316,696 B2 | 1/2008 | Wilson, Jr. et al. |
| 7,585,304 B2 | 9/2009 | Hughett |
| 7,819,886 B2 | 10/2010 | Whitfield et al. |
| 7,905,890 B2 | 3/2011 | Whitfield et al. |
| 8,048,088 B2 | 11/2011 | Green et al. |
| 8,056,565 B2 | 11/2011 | Zergiebel |
| 8,075,571 B2 | 12/2011 | Vitali et al. |
| 8,216,257 B2 | 7/2012 | Huitema et al. |
| 8,236,012 B2 | 8/2012 | Molitor et al. |
| 8,246,634 B2 | 8/2012 | Huitema et al. |
| 8,246,635 B2 | 8/2012 | Huitema |
| 8,328,822 B2 | 12/2012 | Huitema et al. |
| 8,403,138 B2 | 3/2013 | Weisshaupt et al. |
| 8,419,752 B2 | 4/2013 | Sorrentino et al. |
| 8,486,091 B2 | 7/2013 | Sorrentino et al. |
| 8,491,608 B2 | 7/2013 | Sorrentino et al. |
| 8,496,673 B2 | 7/2013 | Nguyen et al. |
| 8,506,580 B2 | 8/2013 | Zergiebel et al. |
| 8,753,356 B2 | 6/2014 | Vitali et al. |
| 8,821,516 B2 | 9/2014 | Huitema |
| 8,894,665 B2 | 11/2014 | Sorrentino et al. |
| 8,915,930 B2 | 12/2014 | Huitema et al. |
| 9,282,972 B1 | 3/2016 | Patel et al. |
| 9,445,810 B2 | 9/2016 | Cappola |
| 9,526,565 B2 | 12/2016 | Strobl |
| 9,717,504 B2 | 8/2017 | Huitema |
| 9,782,181 B2 | 10/2017 | Vitali et al. |
| 10,136,939 B2 | 11/2018 | Minnelli et al. |
| 10,231,732 B1 | 3/2019 | Racenet et al. |
| 10,231,735 B2 | 3/2019 | Sorrentino et al. |
| 10,231,738 B2 | 3/2019 | Sorrentino et al. |
| 10,258,346 B2 | 4/2019 | Zergiebel et al. |
| 10,292,712 B2 | 5/2019 | Shankarsetty |
| 10,349,936 B2 | 7/2019 | Rockrohr et al. |
| 10,349,950 B2 | 7/2019 | Aranyi et al. |
| 10,357,250 B2 | 7/2019 | Zammataro |
| 10,363,045 B2 | 7/2019 | Whitfield et al. |
| 10,368,876 B2 | 8/2019 | Bhatnagar et al. |
| 10,390,831 B2 | 8/2019 | Holsten et al. |
| 10,426,489 B2 | 10/2019 | Baril |
| 2001/0047178 A1 | 11/2001 | Peters |
| 2002/0068947 A1 | 6/2002 | Kuhns et al. |
| 2002/0082618 A1 | 6/2002 | Shipp et al. |
| 2002/0087169 A1 | 7/2002 | Brock et al. |
| 2002/0087170 A1 | 7/2002 | Kuhns et al. |
| 2002/0099388 A1 | 7/2002 | Mayenberger |
| 2002/0120279 A1 | 8/2002 | Deguillebon et al. |
| 2002/0123742 A1 | 9/2002 | Baxter et al. |

(56) References Cited

U.S. PATENT DOCUMENTS

| | | |
|---|---|---|
| 2002/0128668 A1 | 9/2002 | Manetakis et al. |
| 2002/0177859 A1 | 11/2002 | Monassevitch et al. |
| 2002/0198537 A1 | 12/2002 | Smith et al. |
| 2002/0198538 A1 | 12/2002 | Kortenbach et al. |
| 2002/0198539 A1 | 12/2002 | Sixto et al. |
| 2002/0198540 A1 | 12/2002 | Smith et al. |
| 2002/0198541 A1 | 12/2002 | Smith et al. |
| 2003/0014060 A1 | 1/2003 | Wilson, Jr. et al. |
| 2003/0018345 A1 | 1/2003 | Green |
| 2003/0023249 A1 | 1/2003 | Manetakis |
| 2003/0040759 A1 | 2/2003 | de Guillebon et al. |
| 2003/0105476 A1 | 6/2003 | Sancoff et al. |
| 2003/0114867 A1 | 6/2003 | Bolduc et al. |
| 2003/0135224 A1 | 7/2003 | Blake |
| 2003/0167063 A1 | 9/2003 | Kerr |
| 2003/0225423 A1 | 12/2003 | Huitema |
| 2003/0233105 A1 | 12/2003 | Gayton |
| 2004/0010272 A1 | 1/2004 | Manetakis et al. |
| 2004/0097970 A1 | 5/2004 | Hughett |
| 2004/0097971 A1 | 5/2004 | Hughett |
| 2004/0138681 A1 | 7/2004 | Pier |
| 2004/0153100 A1 | 8/2004 | Ahlberg et al. |
| 2005/0080440 A1 | 4/2005 | Durgin et al. |
| 2005/0085830 A1 | 4/2005 | Lehman et al. |
| 2005/0090837 A1 | 4/2005 | Sixto et al. |
| 2005/0090838 A1 | 4/2005 | Sixto et al. |
| 2005/0096670 A1 | 5/2005 | Wellman et al. |
| 2005/0096671 A1 | 5/2005 | Wellman et al. |
| 2005/0096672 A1 | 5/2005 | Manetakis et al. |
| 2005/0101975 A1 | 5/2005 | Nguyen et al. |
| 2005/0107807 A1 | 5/2005 | Nakao |
| 2005/0107809 A1 | 5/2005 | Litscher et al. |
| 2005/0107810 A1 | 5/2005 | Morales et al. |
| 2005/0107811 A1 | 5/2005 | Starksen et al. |
| 2005/0107812 A1 | 5/2005 | Starksen et al. |
| 2005/0107871 A1 | 5/2005 | Realyvasquez et al. |
| 2005/0113847 A1 | 5/2005 | Gadberry et al. |
| 2005/0119671 A1 | 6/2005 | Reydel et al. |
| 2005/0119673 A1 | 6/2005 | Gordon et al. |
| 2005/0119677 A1 | 6/2005 | Shipp |
| 2005/0125010 A1 | 6/2005 | Smith et al. |
| 2005/0143767 A1 | 6/2005 | Kimura et al. |
| 2005/0149063 A1 | 7/2005 | Young et al. |
| 2005/0149064 A1 | 7/2005 | Peterson et al. |
| 2005/0149068 A1 | 7/2005 | Williams et al. |
| 2005/0149069 A1 | 7/2005 | Bertolero et al. |
| 2005/0165415 A1 | 7/2005 | Wales |
| 2005/0165418 A1 | 7/2005 | Chan |
| 2005/0171560 A1 | 8/2005 | Hughett |
| 2005/0177176 A1 | 8/2005 | Gerbi et al. |
| 2005/0177177 A1 | 8/2005 | Viola |
| 2005/0203547 A1 | 9/2005 | Weller et al. |
| 2005/0203548 A1 | 9/2005 | Weller et al. |
| 2005/0216036 A1 | 9/2005 | Nakao |
| 2005/0216056 A1 | 9/2005 | Valdevit et al. |
| 2005/0222588 A1 | 10/2005 | Vandenbroek et al. |
| 2005/0222590 A1 | 10/2005 | Gadberry et al. |
| 2005/0222665 A1 | 10/2005 | Aranyi |
| 2005/0228411 A1 | 10/2005 | Manzo |
| 2005/0228416 A1 | 10/2005 | Burbank et al. |
| 2005/0234478 A1 | 10/2005 | Wixey et al. |
| 2005/0251183 A1 | 11/2005 | Buckman et al. |
| 2005/0251184 A1 | 11/2005 | Anderson |
| 2005/0256529 A1 | 11/2005 | Yawata et al. |
| 2005/0267495 A1 | 12/2005 | Ginn et al. |
| 2005/0273122 A1 | 12/2005 | Theroux et al. |
| 2005/0277951 A1 | 12/2005 | Smith et al. |
| 2005/0277952 A1 | 12/2005 | Arp et al. |
| 2005/0277953 A1 | 12/2005 | Francese et al. |
| 2005/0277954 A1 | 12/2005 | Smith et al. |
| 2005/0277955 A1 | 12/2005 | Palmer et al. |
| 2005/0277956 A1 | 12/2005 | Francese et al. |
| 2005/0277958 A1 | 12/2005 | Levinson |
| 2005/0288689 A1 | 12/2005 | Kammerer et al. |
| 2005/0288690 A1 | 12/2005 | Bourque et al. |
| 2006/0004388 A1 | 1/2006 | Whayne et al. |
| 2006/0004390 A1 | 1/2006 | Rosenberg et al. |
| 2006/0009789 A1 | 1/2006 | Gambale et al. |
| 2006/0009790 A1 | 1/2006 | Blake et al. |
| 2006/0009792 A1 | 1/2006 | Baker et al. |
| 2006/0020270 A1 | 1/2006 | Jabba et al. |
| 2006/0020271 A1 | 1/2006 | Stewart et al. |
| 2006/0047305 A1 | 3/2006 | Ortiz et al. |
| 2006/0047306 A1 | 3/2006 | Ortiz et al. |
| 2006/0064117 A1 | 3/2006 | Aranyi et al. |
| 2006/0079115 A1 | 4/2006 | Aranyi |
| 2006/0079912 A1 | 4/2006 | Whitfield et al. |
| 2006/0079913 A1 | 4/2006 | Whitfield et al. |
| 2006/0085015 A1 | 4/2006 | Whitfield et al. |
| 2006/0085021 A1 | 4/2006 | Wenzler |
| 2006/0100649 A1 | 5/2006 | Hart |
| 2006/0111731 A1 | 5/2006 | Manzo |
| 2006/0124485 A1 | 6/2006 | Kennedy |
| 2006/0129170 A1 | 6/2006 | Royce et al. |
| 2006/0163312 A1 | 7/2006 | Viola et al. |
| 2006/0173470 A1 | 8/2006 | Oray et al. |
| 2006/0178683 A1 | 8/2006 | Shimoji et al. |
| 2006/0184182 A1 | 8/2006 | Aranyi et al. |
| 2006/0190013 A1 | 8/2006 | Menn |
| 2006/0195125 A1 | 8/2006 | Sakakine et al. |
| 2006/0200179 A1 | 9/2006 | Barker et al. |
| 2006/0217749 A1 | 9/2006 | Wilson et al. |
| 2006/0224170 A1 | 10/2006 | Duff |
| 2006/0235437 A1 | 10/2006 | Vitali et al. |
| 2006/0235438 A1 | 10/2006 | Huitema et al. |
| 2006/0235439 A1 | 10/2006 | Molitor et al. |
| 2006/0235440 A1 | 10/2006 | Huitema et al. |
| 2006/0235441 A1 | 10/2006 | Huitema et al. |
| 2006/0235442 A1 | 10/2006 | Huitema |
| 2006/0235443 A1 | 10/2006 | Huitema et al. |
| 2006/0235444 A1 | 10/2006 | Huitema et al. |
| 2006/0259045 A1 | 11/2006 | Damarati |
| 2006/0259049 A1 | 11/2006 | Harada et al. |
| 2006/0264987 A1 | 11/2006 | Sgro |
| 2006/0271072 A1 | 11/2006 | Hummel et al. |
| 2007/0016228 A1 | 1/2007 | Salas |
| 2007/0021761 A1 | 1/2007 | Phillips |
| 2007/0023476 A1 | 2/2007 | Whitman et al. |
| 2007/0023477 A1 | 2/2007 | Whitman et al. |
| 2007/0027458 A1 | 2/2007 | Sixto, Jr. et al. |
| 2007/0034669 A1 | 2/2007 | de la Torre et al. |
| 2007/0038233 A1 | 2/2007 | Martinez et al. |
| 2007/0049947 A1 | 3/2007 | Menn et al. |
| 2007/0049948 A1 | 3/2007 | Menn et al. |
| 2007/0049949 A1 | 3/2007 | Manetakis |
| 2007/0049950 A1 | 3/2007 | Theroux et al. |
| 2007/0049951 A1 | 3/2007 | Menn |
| 2007/0049953 A2 | 3/2007 | Shimoji et al. |
| 2007/0073314 A1 | 3/2007 | Gadberry et al. |
| 2007/0083218 A1 | 4/2007 | Morris |
| 2007/0093856 A1 | 4/2007 | Whitfield et al. |
| 2007/0106314 A1 | 5/2007 | Dunn |
| 2007/0112365 A1 | 5/2007 | Hilal et al. |
| 2007/0118161 A1 | 5/2007 | Kennedy et al. |
| 2007/0118163 A1 | 5/2007 | Boudreaux et al. |
| 2007/0118174 A1 | 5/2007 | Chu |
| 2007/0123916 A1 | 5/2007 | Maier et al. |
| 2007/0142848 A1 | 6/2007 | Ainsworth et al. |
| 2007/0142851 A1 | 6/2007 | Sixto et al. |
| 2007/0149988 A1 | 6/2007 | Michler et al. |
| 2007/0149989 A1 | 6/2007 | Santilli et al. |
| 2007/0162060 A1 | 7/2007 | Wild |
| 2007/0185504 A1 | 8/2007 | Manetakis et al. |
| 2007/0191868 A1 | 8/2007 | Theroux et al. |
| 2007/0213747 A1 | 9/2007 | Monassevitch et al. |
| 2007/0250080 A1 | 10/2007 | Jones et al. |
| 2007/0265640 A1 | 11/2007 | Kortenbach et al. |
| 2007/0276417 A1 | 11/2007 | Mendes, Jr. et al. |
| 2007/0282355 A1 | 12/2007 | Brown et al. |
| 2007/0293875 A1 | 12/2007 | Soetikno et al. |
| 2008/0004636 A1 | 1/2008 | Walberg et al. |
| 2008/0004637 A1 | 1/2008 | Klassen et al. |
| 2008/0004639 A1 | 1/2008 | Huitema et al. |
| 2009/0204115 A1 | 8/2009 | Dees, Jr. et al. |

(56) References Cited

U.S. PATENT DOCUMENTS

| | | |
|---|---|---|
| 2009/0261142 A1 | 10/2009 | Milliman et al. |
| 2009/0264904 A1 | 10/2009 | Aldrich et al. |
| 2009/0299382 A1* | 12/2009 | Zergiebel ............... A61B 34/76 606/142 |
| 2009/0312775 A1 | 12/2009 | Gilkey et al. |
| 2010/0089970 A1 | 4/2010 | Smith et al. |
| 2010/0331862 A1 | 12/2010 | Monassevitch et al. |
| 2011/0087220 A1 | 4/2011 | Felder et al. |
| 2011/0087268 A1 | 4/2011 | Livneh |
| 2012/0022526 A1 | 1/2012 | Aldridge et al. |
| 2013/0041379 A1 | 2/2013 | Bodor et al. |
| 2013/0325057 A1 | 12/2013 | Larson et al. |
| 2014/0188159 A1 | 7/2014 | Steege |
| 2014/0371728 A1 | 12/2014 | Vaughn |
| 2015/0201953 A1 | 7/2015 | Strobl et al. |
| 2015/0265282 A1 | 9/2015 | Miles et al. |
| 2015/0313452 A1 | 11/2015 | Hasser et al. |
| 2015/0314451 A1 | 11/2015 | Nixon |
| 2016/0004956 A1 | 1/2016 | Reynolds et al. |
| 2017/0202567 A1 | 7/2017 | Griffiths et al. |
| 2017/0245921 A1 | 8/2017 | Joseph et al. |
| 2017/0252042 A1 | 9/2017 | Kethman et al. |
| 2017/0290587 A1 | 10/2017 | Schober et al. |
| 2018/0021041 A1 | 1/2018 | Zhang et al. |
| 2018/0263624 A1 | 9/2018 | Malkowski et al. |
| 2018/0325519 A1 | 11/2018 | Baril et al. |
| 2019/0000449 A1 | 1/2019 | Baril et al. |
| 2019/0000482 A1 | 1/2019 | Hu et al. |
| 2019/0000584 A1 | 1/2019 | Baril |
| 2019/0021738 A1 | 1/2019 | Hartoumbekis |
| 2019/0038375 A1 | 2/2019 | Baril et al. |
| 2019/0046202 A1 | 2/2019 | Baril et al. |
| 2019/0046203 A1 | 2/2019 | Baril et al. |
| 2019/0046207 A1 | 2/2019 | Czernik et al. |
| 2019/0046208 A1 | 2/2019 | Baril et al. |
| 2019/0053806 A1 | 2/2019 | Zhang et al. |
| 2019/0053808 A1 | 2/2019 | Baril et al. |
| 2019/0059904 A1 | 2/2019 | Zammataro |
| 2019/0076147 A1 | 3/2019 | Baril et al. |
| 2019/0076148 A1 | 3/2019 | Baril et al. |
| 2019/0076149 A1 | 3/2019 | Baril et al. |
| 2019/0076150 A1 | 3/2019 | Gokharu |
| 2019/0076210 A1 | 3/2019 | Baril et al. |
| 2019/0133583 A1 | 5/2019 | Baril et al. |
| 2019/0133584 A1 | 5/2019 | Baril et al. |
| 2019/0133593 A1 | 5/2019 | P V R |
| 2019/0133594 A1 | 5/2019 | Dinino et al. |
| 2019/0133595 A1 | 5/2019 | Baril et al. |
| 2019/0150935 A1 | 5/2019 | Raikar et al. |
| 2019/0175176 A1 | 6/2019 | Zammataro |
| 2019/0175187 A1 | 6/2019 | P V R |
| 2019/0175188 A1 | 6/2019 | P V R |
| 2019/0175189 A1 | 6/2019 | P V R |
| 2019/0192139 A1 | 6/2019 | Rockrohr et al. |
| 2019/0209177 A1 | 7/2019 | Whitfield et al. |
| 2019/0216464 A1 | 7/2019 | Baril et al. |
| 2019/0239893 A1 | 8/2019 | Shankarsetty |

FOREIGN PATENT DOCUMENTS

| | | |
|---|---|---|
| EP | 0755655 A2 | 1/1997 |
| EP | 0769274 A1 | 4/1997 |
| EP | 0769275 A1 | 4/1997 |
| EP | 0834286 A1 | 4/1998 |
| EP | 1317906 A1 | 6/2003 |
| EP | 1609427 A1 | 12/2005 |
| EP | 1712191 A2 | 10/2006 |
| EP | 1813199 A1 | 8/2007 |
| EP | 1908423 A2 | 4/2008 |
| EP | 1913881 A1 | 4/2008 |
| EP | 2158851 A1 | 3/2010 |
| EP | 3132756 A1 | 2/2017 |
| JP | 2011186812 A | 9/2011 |
| JP | 2013166982 A | 8/2013 |
| WO | 9003763 A1 | 4/1990 |
| WO | 2005091457 A1 | 9/2005 |
| WO | 2006042076 A2 | 4/2006 |
| WO | 2006042084 A2 | 4/2006 |
| WO | 2006042110 A2 | 4/2006 |
| WO | 2008118928 A2 | 10/2008 |
| WO | 2008127968 A2 | 10/2008 |
| WO | 2017084000 A1 | 5/2017 |
| WO | 2017146138 A1 | 8/2017 |
| WO | 2018141110 A1 | 8/2018 |
| WO | 2019055359 A1 | 3/2019 |

OTHER PUBLICATIONS

International Search Report corresponding to Int'l Patent Appln. PCT/US2018/050316 dated Dec. 31, 2018.
International Search Report corresponding to Int'l Patent Appln. PCT/US2018/050336 dated Jan. 7, 2019.
International Search Report corresponding to Int'l Patent Appln. PCT/US2018/050325 dated Jan. 7, 2019.
International Search Report corresponding to Int'l Patent Appln. PCT/US2018/045306 dated Jan. 16, 2019.
International Search Report corresponding to Int'l Patent Appln. PCT/US2018/050349 dated Jan. 21, 2019.
International Search Report corresponding to Int'l Patent Appln. PCT/US2018/045725 dated Jan. 28, 2019.
Extended European Search Report corresponding to European Patent Application EP 18208630.6 dated Feb. 12, 2019.
International Search Report corresponding to Int'l Patent Appln. PCT/US2018/057910 dated Feb. 22, 2019.
International Search Report corresponding to Int'l Patent Appln. PCT/US2018/057922 dated Feb. 22, 2019.
International Search Report corresponding to Int'l Patent Appln. PCT/US2018/058078 dated Feb. 22, 2019.
International Search Report corresponding to Int'l Patent Appln. PCT/US2018/058603 dated Feb. 22, 2019.
International Search Report corresponding to Int'l Patent Appln. PCT/US2018/057221 dated Mar. 11, 2019.
Extended European Search Report corresponding to European Patent Application EP 18212043.6 dated Apr. 24, 2019.
Extended European Search Report corresponding to European Patent Application EP 18211565.9 dated Apr. 26, 2019.
Extended European Search Report corresponding to European Patent Application EP 18211921.4 dated Apr. 30, 2019.
Chinese First Office Action corresponding to Chinese Patent Application CN 201510868226.8 dated May 29, 2019.
Extended European Search Report corresponding to European Patent Application EP 15905685.2 dated May 29, 2019.
European Office Action corresponding to European Patent Application EP 17157606.9 dated Jul. 2, 2019.
Extended European Search Report corresponding to European Patent Application EP 15908025.8 dated Jul. 2, 2019.
Extended European Search Report corresponding to European Patent Application EP 18212054.3 dated Jul. 3, 2019.
Partial Supplementary European Search Report corresponding to European Patent Application EP 16884297.9 dated Jul. 30, 2019.

* cited by examiner

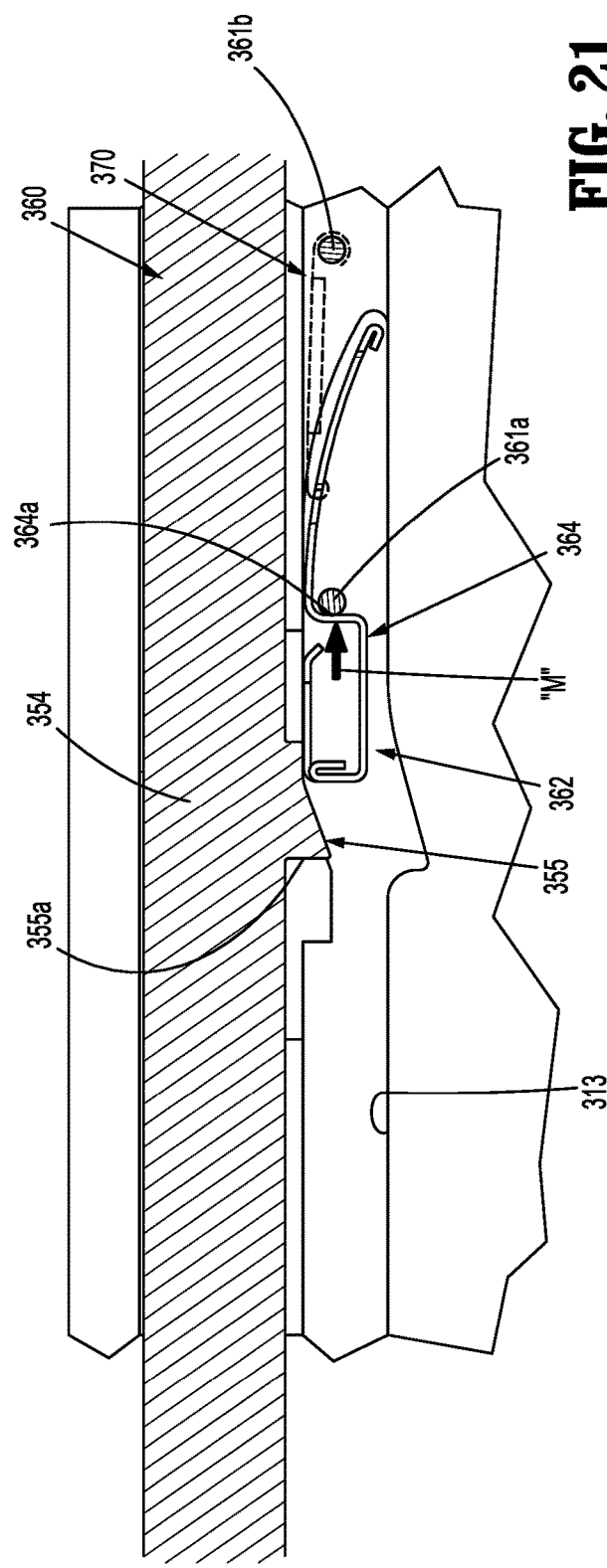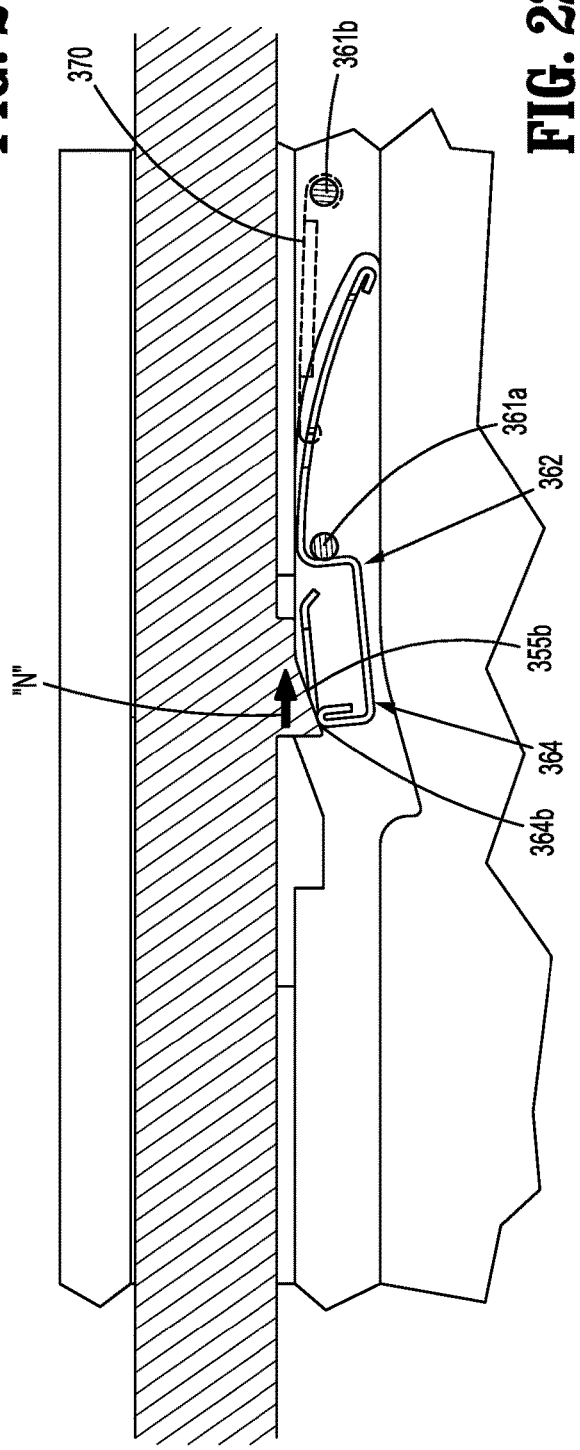

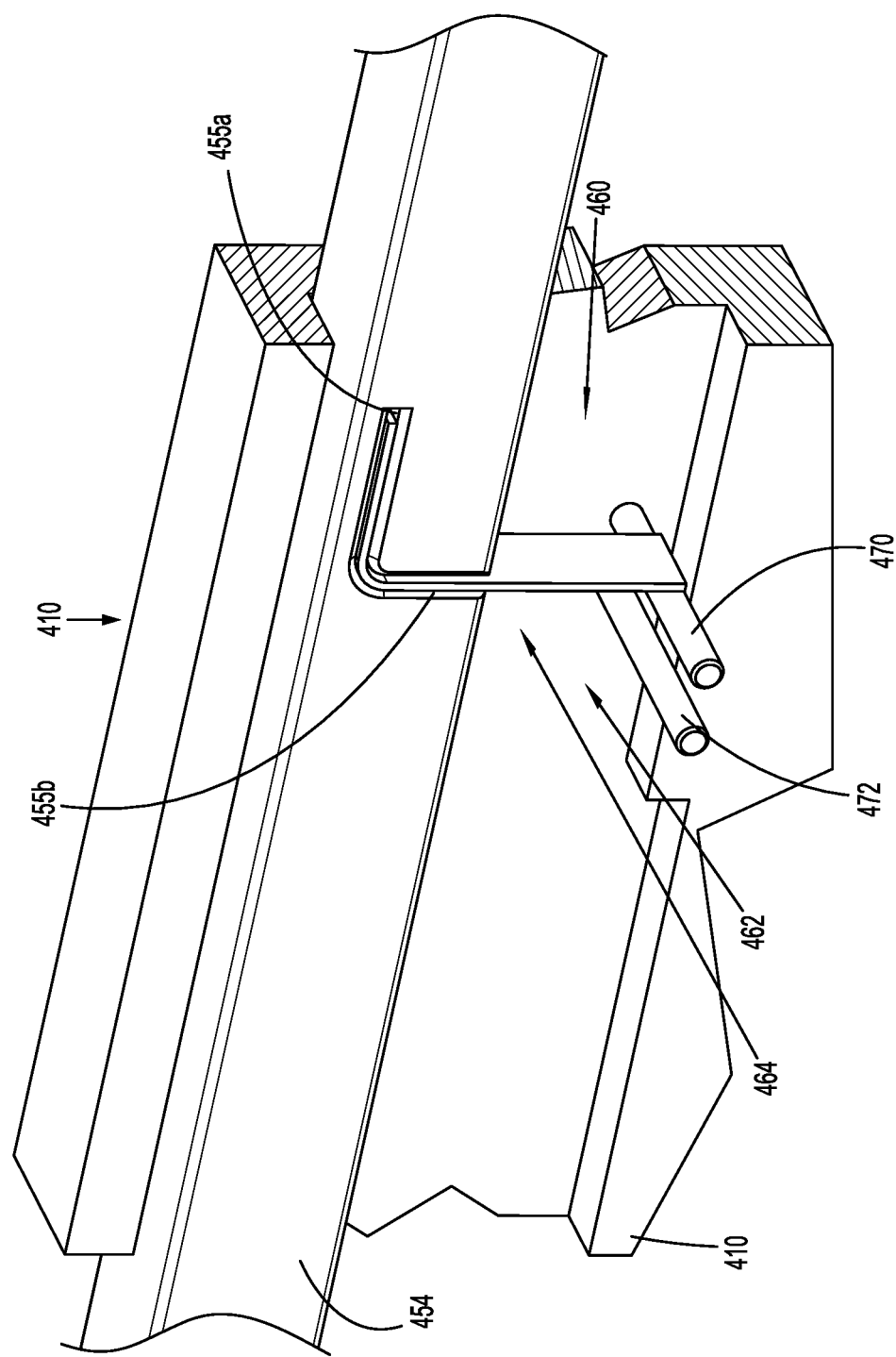

FEEDBACK MECHANISMS FOR HANDLE ASSEMBLIES

CROSS-REFERENCE TO RELATED APPLICATION

This application claims the benefit of and priority to U.S. Provisional Patent Application No. 62/717,023 filed Aug. 10, 2018, the entire disclosure of which is incorporated by reference herein.

BACKGROUND

Technical Field

The present disclosure relates to handle assemblies for surgical instruments. More particularly, the present disclosure relates to mechanisms for providing feedback to a user to indicate full or complete actuation of the handle assembly.

Description of Related Art

Reusable handle assemblies are known in the art medical and are used for a number of distinct and useful surgical procedures. In the case of a laparoscopic surgical procedure, access to the interior of an abdomen is achieved through narrow tubes or cannulas that are releasably secured to the reusable handles inserted through a small entrance incision in the skin. Minimally invasive procedures performed elsewhere in the body are often generally referred to as endoscopic procedures.

During, for example, a surgical procedure using a clip applier, clip formation occurs upon completion of a firing stroke. To ensure clip formation, it would be beneficial to have a handle assembly with an audible and/or tactile feedback mechanism to signal to a user when the actuation stroke is complete.

SUMMARY

A handle assembly for actuating an end effector is provided. The handle assembly includes a housing defining a longitudinal axis, a trigger operably coupled to the housing and movable to cause actuation of the handle assembly, a drive member movable within the housing from an initial position to an advanced position in response to actuation of the trigger, and a feedback mechanism in operable engagement with the trigger. The feedback mechanism includes a torsion spring having a hammer portion. Upon full actuation of the handle assembly, the hammer portion of the torsion spring strikes a surface to create at least one of an audible or a tactile response.

In embodiments, the housing includes a body portion and a trigger portion. The feedback mechanism may include a ramp portion. The hammer portion of the torsion spring may engage the ramp portion during actuation of the handle assembly to transition the torsion spring to a loaded condition. Upon complete actuation of the handle assembly, the hammer portion of the torsion spring may disengage the ramp portion to unload the torsion spring. Upon unloading of the torsion spring, the hammer portion may strike the surface to create the at least one audible or tactile response.

A first end of the torsion spring may be secured relative to the trigger. When secured relative to the trigger, the torsion spring may include a spring portion which may be received about a pivot pin secured to the trigger. An end of the torsion spring may be secured to the housing. When secured to the housing, the torsion spring may include a spring portion which may be received about a pivot pin secured to the housing. The torsion spring may be moved to a loaded condition during actuation of the handle assembly.

Another handle assembly for actuating an end effector is provided. The handle assembly includes a housing defining a longitudinal axis, a trigger operably coupled to the housing and movable to cause actuation of the handle assembly, and a drive member movable within the housing from an initial position to an advanced position in response to actuation of the trigger. The drive member includes a ramp portion. The handle assembly further includes a feedback mechanism including a hammer member in selective engagement with the ramp portion of the drive member. Upon complete actuation of the handle assembly, the hammer member disengages from the ramp portion and strikes a first pin to create at least one of an audible or a tactile response.

Movement of the drive member from the initial position to the advanced position may cause the hammer member to move from a first position to a second position and back to the first position. Return of the hammer member to the first position may create the at least one audible or tactile response. The feedback mechanism further includes a tension spring, the tension spring being secured to the hammer member and configured to bias the hammer member to the first position. Return of the drive member to the initial position may reengage the hammer member with the ramp portion.

Another handle assembly for actuating an end effector is provided. The handle assembly includes a housing defining a longitudinal axis, a trigger operably coupled to the housing and movable to cause actuation of the handle assembly, and a drive member movable within the housing from an initial position to an advanced position in response to actuation of the trigger. The drive member includes a ramp portion. The handle assembly further includes a feedback mechanism having first and second pins disposed within the housing, and a spring member secured to the drive member. The spring member is configured to engage the first pin during the actuation of the handle assembly and disengage from the first pin upon full actuation of the handle assembly.

In embodiments, the spring member is configured to engage the second pin upon disengagement from first pin to create a least one of an audible or tactile response. The spring member may include a torsion spring. The spring member may transition to a loaded condition during movement of the drive member from the initial position to the advanced position.

BRIEF DESCRIPTION OF THE DRAWINGS

Aspects and features of the present disclosure are described in detail with reference to the drawing figures wherein like reference numerals identify similar or identical structural elements and:

FIG. 21 is a cross-sectional side view taken along line 19-19 shown in FIG. 16, with the drive bar in a fully advanced position;

FIG. 22 is a cross-sectional side view taken along line 19-19 shown in FIG. 16, with the drive bar in a partially retracted position;

FIG. 23 is a perspective view of a feedback mechanism according to yet another embodiment of the present disclosure;

DETAILED DESCRIPTION

Figure 1:
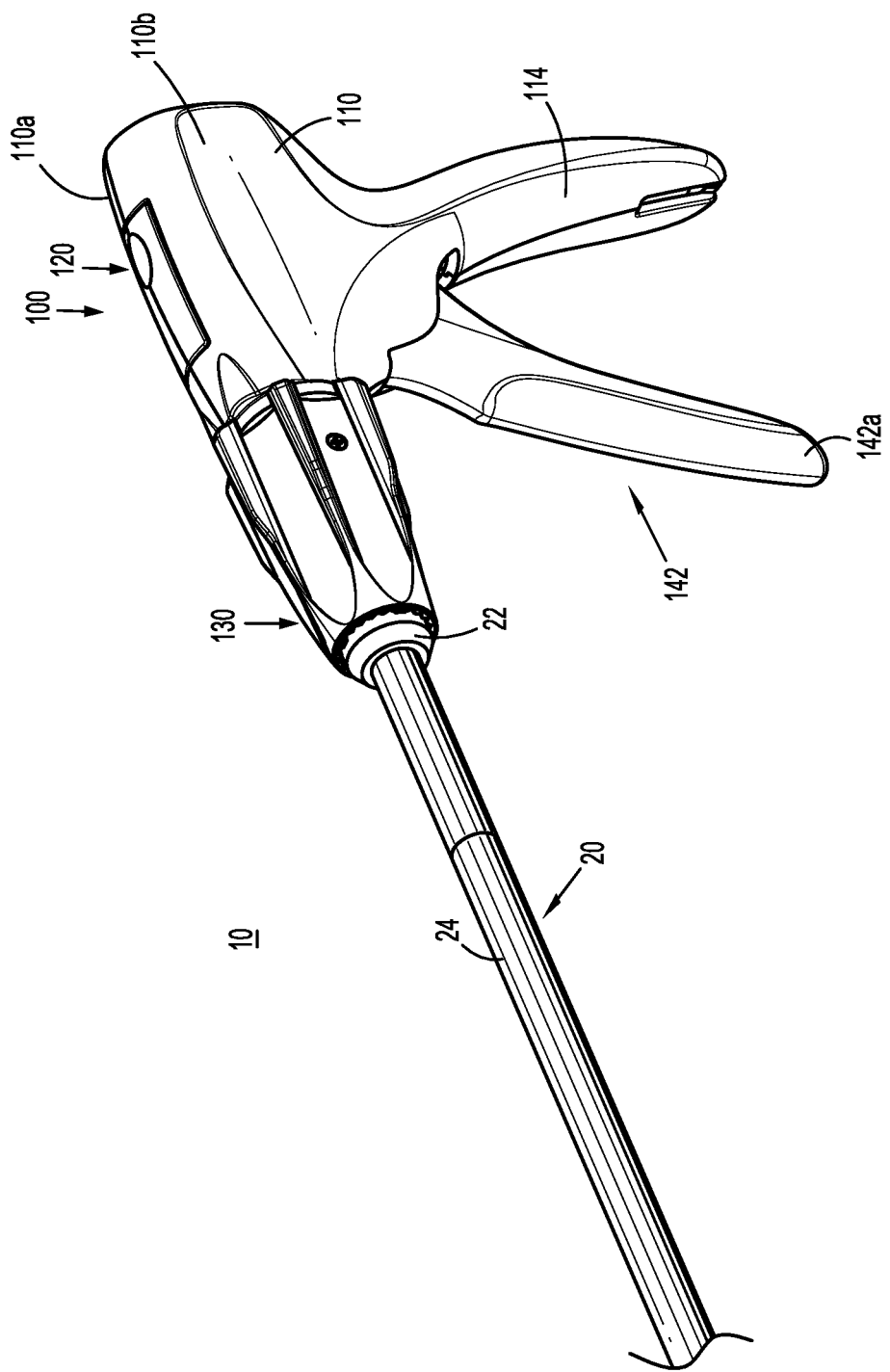
FIG. 1 is a front, perspective view of a surgical clip applier according to an embodiment of the present disclosure including a handle assembly having an elongated assembly engaged therewith.

As detailed herein and shown in the drawing figures, as is traditional when referring to relative positioning on a surgical instrument, the term "proximal" refers to the end of the apparatus or component thereof which is closer to the user and the term "distal" refers to the end of the apparatus or component thereof which is farther away from the user. Further, to the extent consistent, any or all of the aspects and features detailed herein may be used in conjunction with any or all of the other aspects and features detailed herein.

The present disclosure provides feedback mechanisms for handle assemblies of surgical instruments. Although detailed herein as incorporated into handle assemblies for surgical clip appliers, the feedback mechanism of the present disclosure may be incorporated into any suitable surgical instrument.

Figure 2:
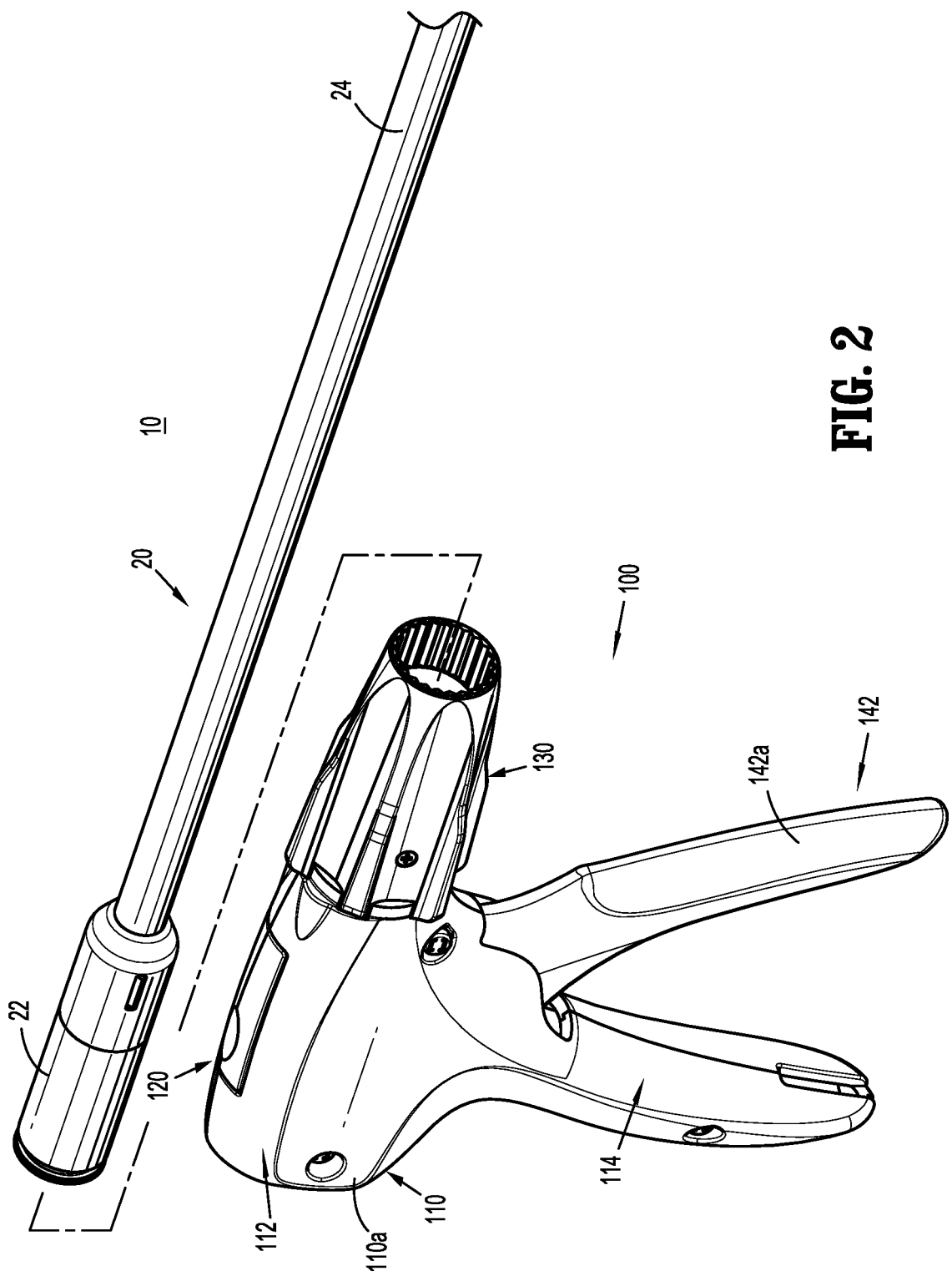
FIG. 2 is front, perspective view of the surgical clip applier with the elongated assembly removed from the handle assembly.

Turning to FIGS. 1 and 2, a surgical clip applier according to aspects of the present disclosure is shown generally as clip applier 10. The clip applier 10 generally includes a handle assembly 100 and an adapter assembly 20 selectively connectable to the handle assembly 100. The handle assembly 100 is configured to operate the adapter assembly 20 upon connection of the adapter assembly 20 to the handle assembly 100, and may be configured as a sterilizable, reusable component such that handle assembly 100 may be repeatedly used with different and/or additional elongated assemblies (not shown) during the course of one or more surgical procedures. The adapter assembly 20 may be configured as a single-use disposable component, limited-use disposable components, or reusable components, depending upon a particular purpose and/or the configuration of the particular adapter assembly. In either configuration, the need for multiple handle assemblies 100 is obviated and, instead, the surgeon need only select an appropriate adapter assembly, and connect that adapter assembly to the handle assembly 100 in preparation for use.

The handle assembly 100 includes a housing 110, a latch assembly 120 (FIG. 3) operably disposed within housing 110, a rotation knob assembly 130 disposed on a distal end of the housing 110, and an actuation mechanism 140 operably disposed within the housing 110. The housing 110 supports and/or encloses the operating components of handle assembly 100. The latch mechanism 120 is configured to facilitate releasable locking engagement of the adapter assembly 20 with the handle assembly 100. The rotation knob assembly 130 enables the selective rotation of the attached adapter assembly 20 relative to the housing 110. The actuation mechanism 140 is configured to enable selective firing of one or more surgical clips (not shown) from an end effector (not shown) of the attached adapter assembly 20.

The handle assembly 100 will only be described to the extent necessary to fully disclose the aspects of the present disclosure. For a detailed description of the operation and function of an exemplary handle assembly, including exemplary latch and rotation knob assemblies, please refer to commonly owned U.S. Pat. App. Pub. No. 2019/0133584, the content of which is incorporated herein by reference in its entirety. Other exemplary embodiments of handle assemblies may be found in commonly owned Intl. Pat. App. Nos. PCT/CN2016/096666 and PCT/CN2016/071178, filed on Aug. 26, 2016 and Jan. 18, 2016, respectively, the content of each is hereby incorporated herein by reference in its entirety.

Referring still to FIGS. 1 and 2, the adapter assembly 20 of the clip applier 10 generally includes a proximal hub 22, an elongated shaft 24 extending distally from the proximal hub 22, an end effector (not shown) disposed towards a distal end portion of the elongated shaft 24, and an inner drive assembly (not shown) operably coupled between the handle assembly 100 and the end effector when adapter assembly 20 is engaged with the handle assembly 100, to enable the sequential firing of at least one surgical clip (not shown) about tissue. The end effector of the adapter assembly 20 may be configured to fire surgical clips similar to those shown and described in U.S. Pat. No. 7,819,886 or 7,905,890, the content of each of which is hereby incorporated herein by reference in its entirety.

Figure 3:
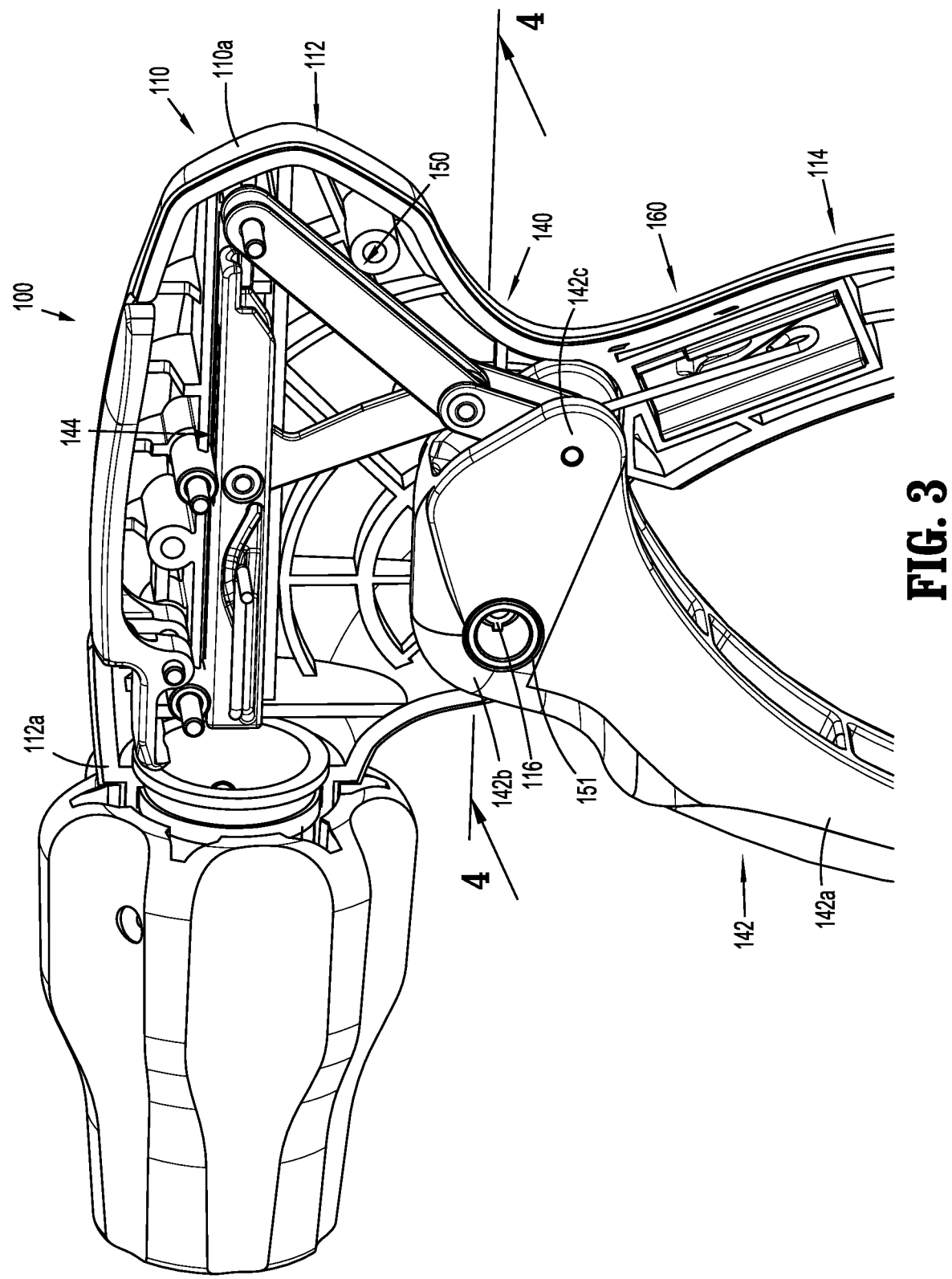
FIG. 3 is a side perspective view of the handle assembly of the surgical clip applier shown in FIGS. 1 and 2, with a housing half removed exposing an actuation assembly including a trigger and a feedback mechanism.
Figure 4:
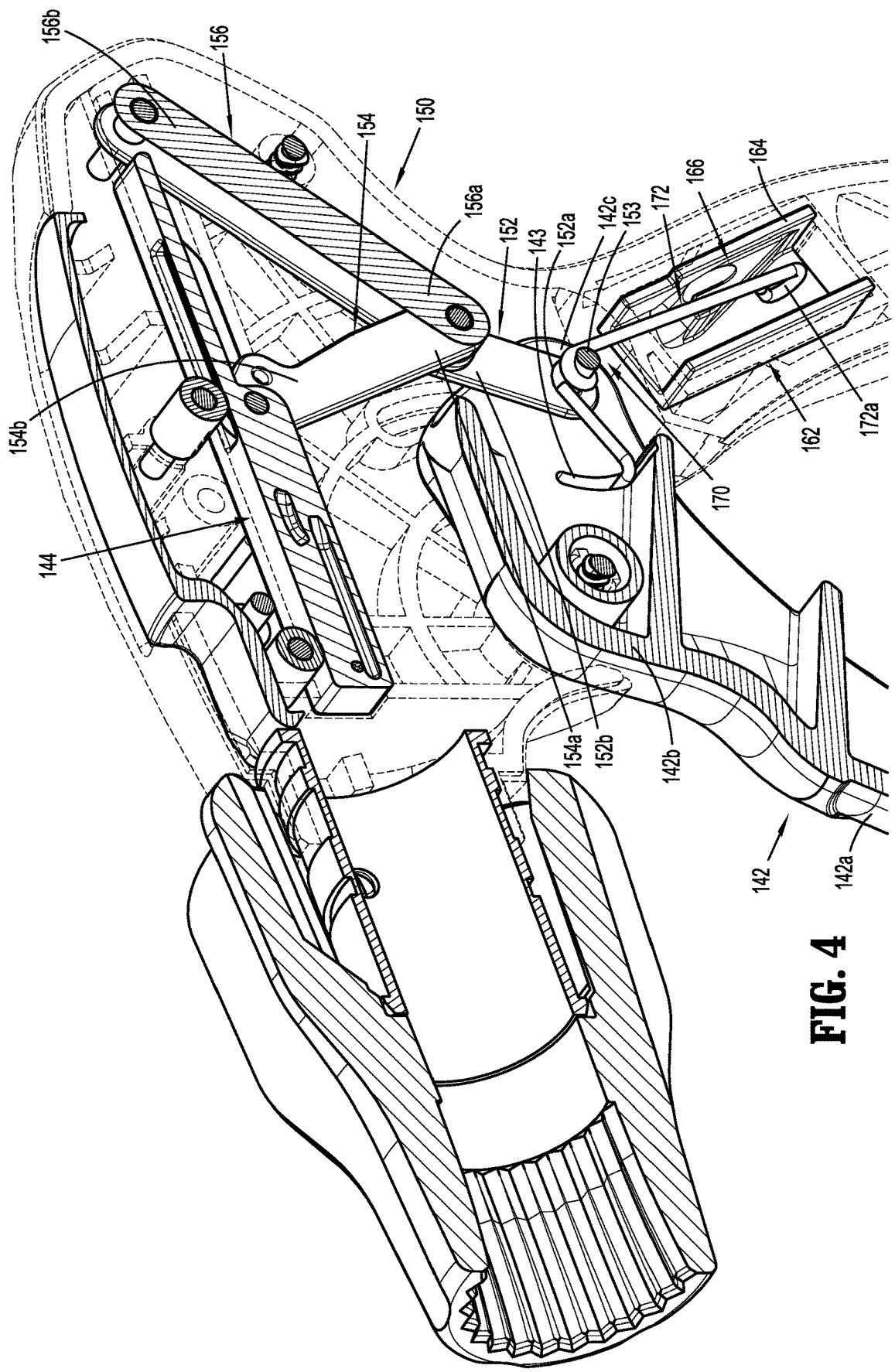
FIG. 4 is a cross-sectional perspective view taken along line 4-4 shown in FIG. 3.

With additional reference to FIG. 3, the housing 110 of the handle assembly 100 may be formed from first and second housing halves 110a, 110b (FIG. 1) that cooperate to define a body portion 112, and a fixed handle portion 114 depending from the body portion 112. A proximal end portion of the proximal hub 22 of the adapter assembly 20 is configured to extend at least partially through an opening in a distal nose 112a of the housing 110 when the adapter assembly 20 (FIG. 1) is engaged with the handle assembly 100. The body portion 112 of housing 110 further includes an internal pivot post 116 extending transversely within body portion 112.

The actuation mechanism 140 of the handle assembly 100 is operably supported by the housing 110 and includes a trigger member 142, a drive bar 144 operably connected to the trigger member 142 by a linkage assembly 150, and a feedback mechanism 160 operably connected to the trigger member 142. As described below, the feedback mechanism 160 produces an audible and/or or tactile response during actuation of the handle assembly 100 to indicate completion of a firing or actuation stroke of the handle assembly 100.

The trigger member 142 of the actuation mechanism 140 includes a grasping portion 142a, an intermediate pivot portion 142b, and a proximal extension 142c. The grasping portion 142a of the trigger member 142 extends downwardly from the body portion 112 of the housing 110 in opposed relation relative to the fixed handle portion 114 of the housing 110. The grasping portion 142a is configured to facilitate grasping and manipulation of the trigger member 142.

The intermediate pivot portion 142b of the trigger member 142 is at least partially disposed within the housing 110 and defines a pivot aperture 151 that is configured to receive the pivot post 116 of the housing 110 so as to enable pivoting of the trigger member 142 about the pivot post 116 and relative to the housing 110, e.g., between an initial or pre-actuated position (FIG. 3), wherein the grasping portion 142a of the trigger member 142 is spaced-apart from the fixed handle portion 114, and a fully actuated position (FIG. 9), wherein the grasping portion 142a of the trigger member 142 is approximated relative to the fixed handle portion 114.

The proximal extension 142c of the trigger member 142 is disposed on an opposite side of the intermediate pivot portion 142b and, thus, opposite the pivot post 116, as compared to the grasping portion 142a of the trigger member 142. As such, pivoting of the grasping portion 142a to rotate in one direction, e.g., proximally towards the fixed handle portion 114, pivots the proximal extension 142c to rotate in the opposite direction, e.g., distally. As described in detail below, the proximal extension 142c of the trigger member 142 defines an arcuate slot 143 for receiving an engagement portion 176 of a torsion spring 170 of the feedback mechanism 160.

The linkage assembly 150 of the actuation assembly 140 includes a first linkage member 152, a second linkage member 154, and a third linkage member 156. A first portion 152a of the first linkage member 152 is pivotally coupled to the proximal extension 142c of the trigger member 142 by a pivot pin 153. The second and third linkages 154, 156, respectively, are each pivotally coupled to a second portion 152b of the first linkage member 152 at respective first portions 154a, 156a of the respective second and third linkages 154, 156. A second portion 154b of the second linkage member 154 is pivotally coupled to the drive bar 144, while a second portion 156b of the third linkage member 156 is pivotally coupled to the body portion 112 of the housing 110. Thus, the pivot point between the first linkage member 152 and the proximal extension 142c of the trigger member 142, the pivot point between the first linkage member 152 and second and third linkages 154, 156, respectively, and the pivot point between the second linkage member 154 and the drive bar 144 are movable pivot points (e.g., movable relative to the housing 110), while the pivot point between the third linkage member 156 and the housing 110 is a fixed pivot point (e.g., fixed relative to the housing 110).

The feedback mechanism 160 of the handle assembly 100 includes a base member 162 and a torsion spring 170. The base member 162 is disposed within the fixed trigger portion 114 of the housing 110 and the torsion spring 170 is operably received about the pivot pin 153 that secures the first linkage 152 to the proximal extension 142c of the trigger member 142. In embodiments, the base member 162 operates in conjunction with the torsion spring 170 to produce an audible sound and/or tactile response/feedback when the trigger member 142 completes a firing stroke.

Figure 5:
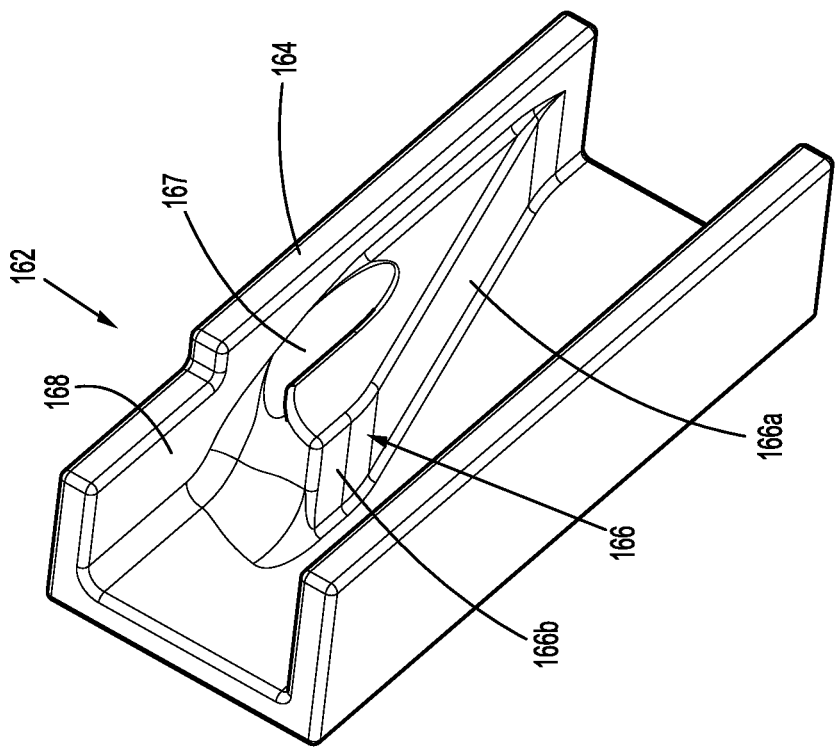
FIG. 5 is a side perspective view of a base member of the feedback mechanism shown in FIG. 3.

With particular reference to FIG. 5, the base member 162 of the feedback mechanism 160 includes a substantially U-shaped body 164 supported within the fixed trigger portion 114 of the housing 110. A ramp portion 166 is disposed within the U-shaped body 164 of the base member 162. The ramp portion 166 includes an inclined surface 166a and an edge surface 166b. The base member 162 includes a sounding surface 168 disposed adjacent the edge surface 166b of the ramp portion 166. As will be described below, a hammer portion 172a of the torsion spring 170 rides along the inclined surface 166a of the ramp portion 166 during actuation of the handle assembly 100, and slides off of the edge surface 166b of the ramp portion 166 and into engagement with the sounding surface 168 upon completion of the firing stroke. The ramp portion 166 of the base member 162 defines a cam track 167 for repositioning the hammer portion 172 of the torsion spring following actuation of the handle assembly 100.

The base member 162 may be formed of metal or plastic. In embodiments, the base member 162 is formed by metal injected molding (MIM).

Figure 6:
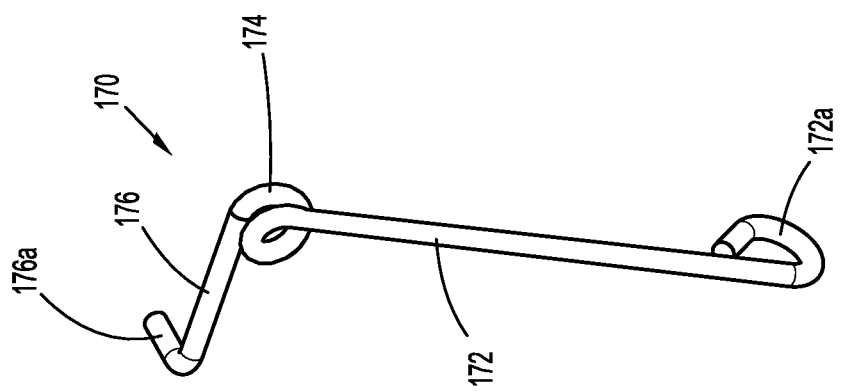
FIG. 6 is a side perspective view of a torsion spring of the feedback mechanism shown in FIG. 3.

Turning now to FIG. 6, the torsion spring 170 of the feedback mechanism includes an elongate body 172 having the hammer portion 172a on a first, free end and a spring portion 174 on a second end. A flange portion 176 extends from the spring portion 174 and includes an engagement portion 176a formed on a free end of the flange portion 176.

Figure 8:
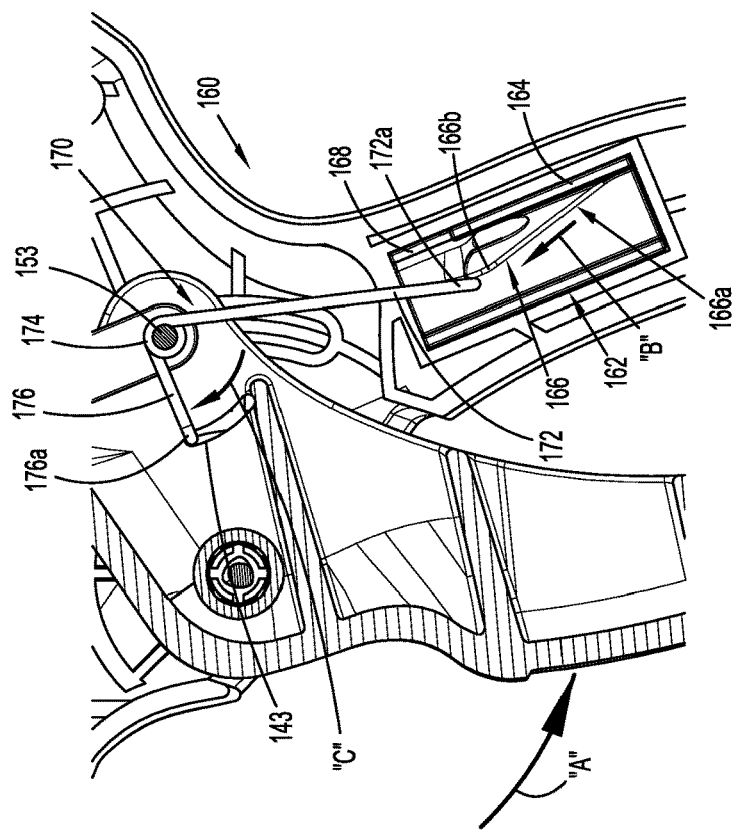
FIG. 8 is a cross-sectional side view taken along line 4-4 shown in FIG. 3 of the handle assembly shown in FIG. 3 with the trigger in a partially actuated position.
Figure 7:
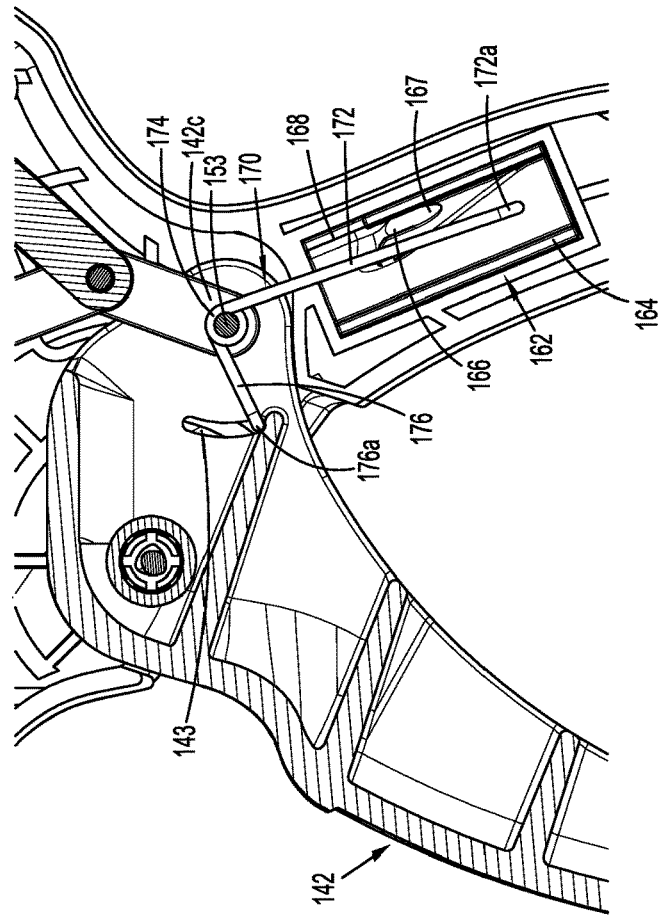
FIG. 7 is a cross-sectional side view taken along line 4-4 shown in FIG. 3, with a trigger in a first or initial position.
Figure 9:
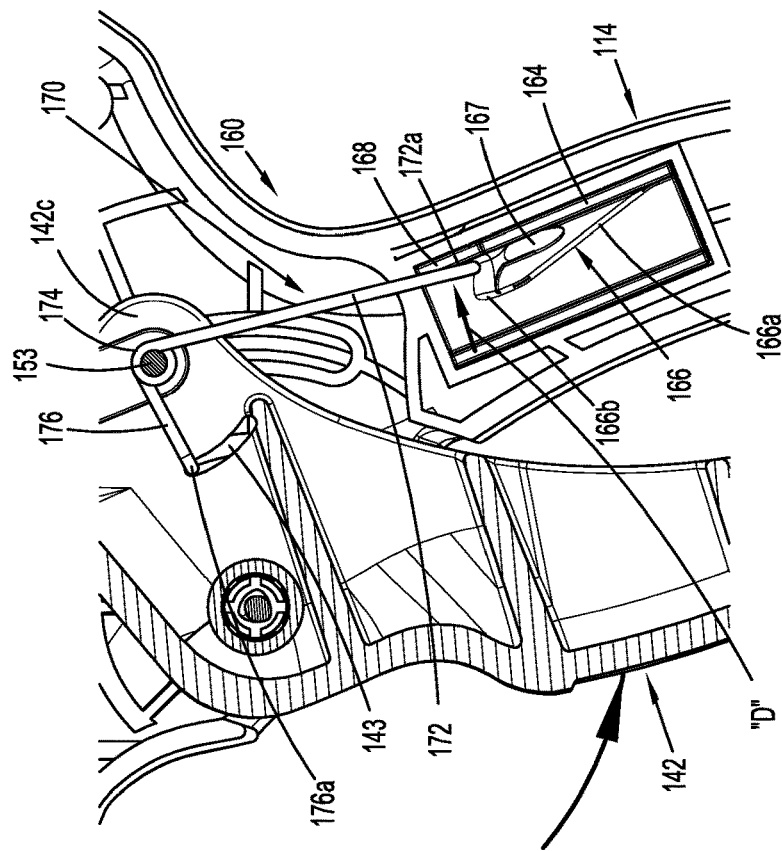
FIG. 9 is a cross-sectional side view taken along line 4-4 shown in FIG. 3 of the handle assembly shown in FIG. 3 with the trigger in a fully actuated position.
Figure 12:
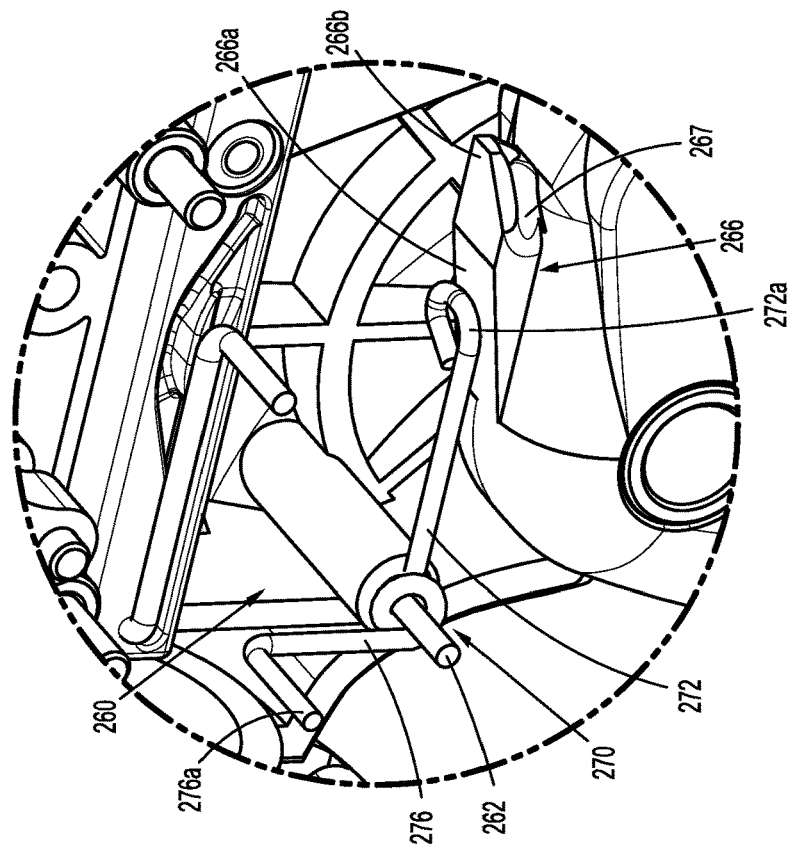
FIG. 12 is an enlarged view of the indicated area of detail shown in FIG. 11.
Figure 11:
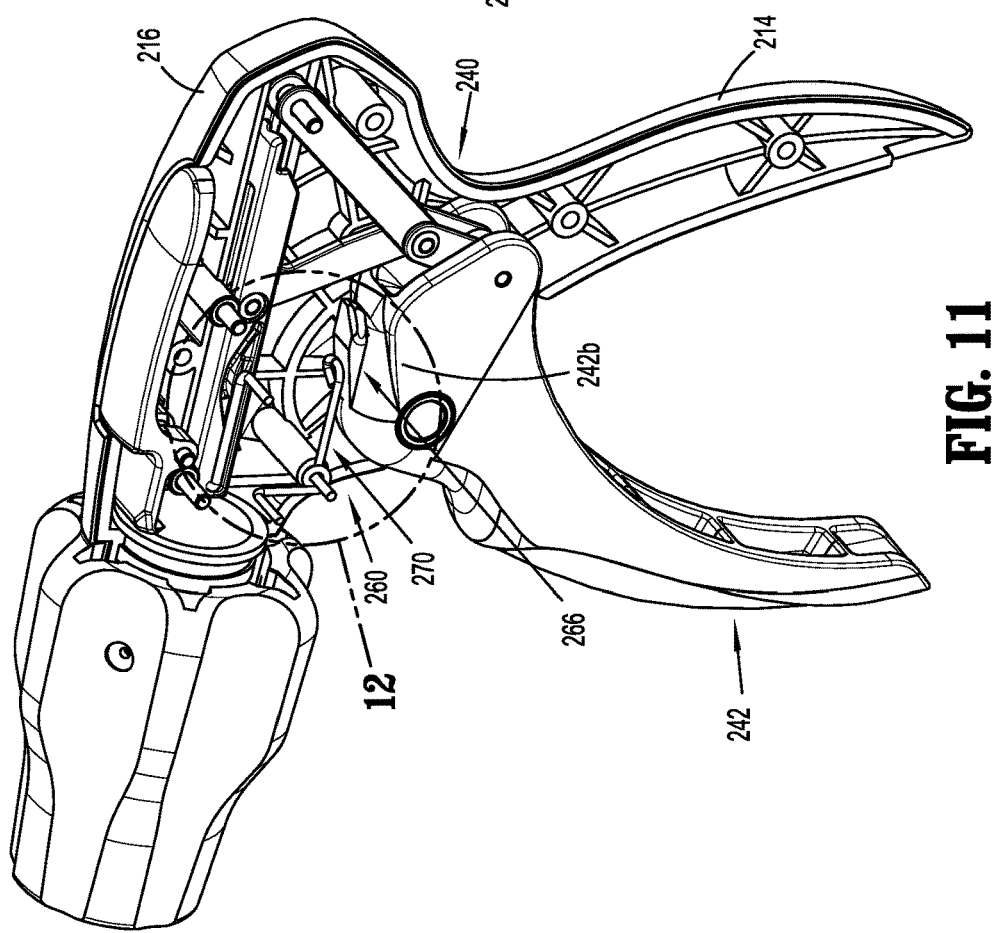
FIG. 11 is a perspective end view of a handle assembly including a feedback mechanism according to another embodiment of the present disclosure.

With additional reference to FIGS. 7-9, the spring portion 174 of the torsion spring 170 of the feedback mechanism 160 is received about the pivot pin 153 that secures the first linkage 152 of the linkage assembly 150 to the proximal extension 142c of the trigger member 142. The elongate portion 172 of the torsion spring 170 is operably received within the base member 162 of the feedback mechanism 160 and the engagement portion 176a of the torsion spring 170 is received within the arcuate slot 143 in the proximal extension 142c of the trigger member 142.

With particular reference to FIG. 8, upon actuation of the trigger member 142, e.g., proximal pivoting of the grasping portion 142a of the trigger member 142 toward the fixed handle portion 114 of the housing 110, as indicated by arrow "A", the proximal extension 142c is moved in a counter-clockwise direction. The counter-clockwise movement of the proximal extension 142c of the trigger member 142 effects movement of the hammer portion 172 on the free end of the elongate body 172 of the torsion spring 170 along the inclined surface 166a of the ramp portion 166 of the base member 162, as indicated by arrow "B". During actuation of the trigger member 142, the engagement portion 176a on the free end of the flange portion 176 of the torsion spring 170 rides along the slot 143 in the proximal extension 142c of the trigger member 142, as indicated by arrow "C", and flexes to cam the spring portion 174 of the torsion spring 170 to a loaded condition.

Turning to FIG. 9, the ramp portion 166 of the base member 162 and the torsion spring 170 of the feedback mechanism 160 are configured such that at the end of the actuation stroke, the hammer portion 172a of the torsion spring 170 disengages from the edge surface 166b of the ramp portion 166. As noted above, during actuation of the trigger member 142, the spring portion 174 is cammed to the loaded condition. In this manner, when the hammer portion 172a of the torsion spring 170 disengages from the edge surface 166b of the ramp portion 166, the hammer portion 172a snaps against the sounding surface 168 of the base member 162, as indicated by arrow "D", thereby producing an audible sound. It is envisioned that the contact of the hammer portion 172a of the torsion spring 170 with the sounding surface 168 may also produce a tactile response, e.g. vibration.

Figure 10:
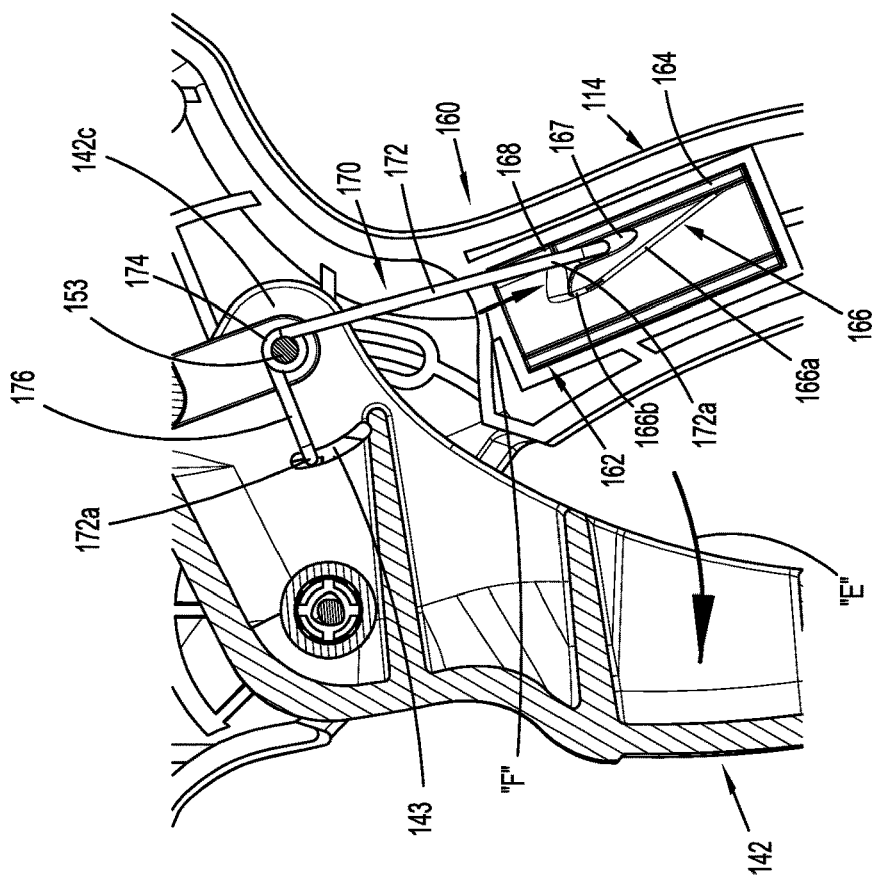
FIG. 10 is a cross-sectional perspective view taken along line 4-4 shown in FIG. 3 of the handle assembly shown in FIG. 3 with the trigger in a partially returned position.

With reference to FIG. 10, as the trigger member 142 returns to its initial position, as indicated by arrow "E", the elongate body 172 of the torsion spring 170 advances within the base member 162, as indicated by arrow "F", such that the hammer portion 172a of the torsion spring engages the cam track 167 of the ramp portion 166. As the hammer portion 172a engages the cam track 167 of the ramp portion 166, the hammer portion 172a is guided past the ramp portion 166 to return to its initial position disposed along the inclined surface 166a of the ramp portion 166, thereby resetting the feedback mechanism 160, and readying the handle assembly 100 for further use.

With reference now to FIGS. 11-15, a reusable handle assembly including a feedback mechanism according to another embodiment of the present disclosure is shown generally as handle assembly 200. The handle assembly 200 is substantially similar to the handle assembly 100 described hereinabove and will only be described in detail as relates to the differences therebetween.

The handle assembly 200 includes a housing 210, a latch assembly 220 operably disposed within the housing 210, a rotation knob assembly 230 dispose on a distal nose 212a of a body portion 212 of the housing 210, and an actuation mechanism 240 operably supported within the housing 210. First and second housing halves 210a (only one shown) of the housing 210 cooperate to define the body portion 212 and a fixed handle portion 214 depending from the body portion 212. The body portion 212 of housing 210 includes an internal pivot post 216 extending transversely within body portion 212.

The actuation mechanism 240 of the handle assembly 200 includes a trigger member 242, a drive bar 244 operably connected to the trigger member 242 by a linkage assembly 250, and a feedback mechanism 260 operably connected to the trigger member 242 to signal completion of a firing stroke. As described below, the feedback mechanism 250 produces an audible and/or tactile feedback during actuation of the handle assembly 200 upon completion of an actuation stroke, e.g., full clip formation.

The trigger member 242 of the actuation mechanism 240 includes a grasping portion 242a, an intermediate pivot portion 242b, and a proximal extension 242c. The intermediate pivot portion 242b of the trigger member 242 is at least partially disposed within the housing 210 and defines a pivot aperture 251 that is configured to receive the pivot post 216 of the housing 210. The trigger member 242 pivots about the pivot post 216 and relative to the housing 210, e.g., between an initial or pre-actuated position (FIG. 11), wherein the grasping portion 242a of the trigger member 242 is spaced-apart relative to the fixed handle portion 214, and an actuated position (FIG. 14), wherein the grasping portion 242a of the trigger member 242 is approximated relative to the fixed handle portion 214.

The feedback mechanism 260 is operably disposed within the body portion 212 of the housing 210 of the handle assembly 200 and includes a ramp portion 266 and a torsion spring 270. More particularly, the ramp portion 266 is formed on an outer surface of the intermediate pivot portion 242b of the trigger member 242 of the actuation assembly 240. The ramp portion 266 includes an inclined surface 266a and an edge surface 266b, and defines a cam track 267. As will be detailed below, during a firing stroke of the handle assembly 200, the ramp portion 266 directs a hammer portion 272a of the torsion spring 270 into a snapping engagement with an outer surface of the intermediate pivot portion 242b of the trigger member 242 to provide an audible and/or tactile response that the handle assembly 200 firing stroke is complete, e.g., the actuation assembly 240 is fully actuated. The ramp portion 266 is configured to reset the hammer portion 272a of the torsion spring 270 as the trigger member 242 returns to its pre-actuated position to permit subsequent firing of the handle assembly 200.

The torsion spring 270 includes an elongate body 272 with the hammer portion 272a disposed on a first, free end and a spring portion 274 on a second end. A flange portion 276 extends from the spring portion 274 and includes an engagement portion 276a formed on a free end of the flange portion 276.

The spring portion 274 of the torsion spring 270 of the feedback mechanism 260 is received by a pivot pin 262 that is supported within the body portion 212 of the housing 210. The elongate portion 272 of the torsion spring 270 extends towards the intermediate pivot portion 242b of the trigger member 242 such that the hammer portion 272a of the torsion spring 270 engages the inclined portion 266a of the ramp portion 266 of the feedback mechanism 260. The engagement portion 276a of the torsion spring 270 engages the body portion 112 of the housing 210 and remains in a fixed position.

Figure 13:
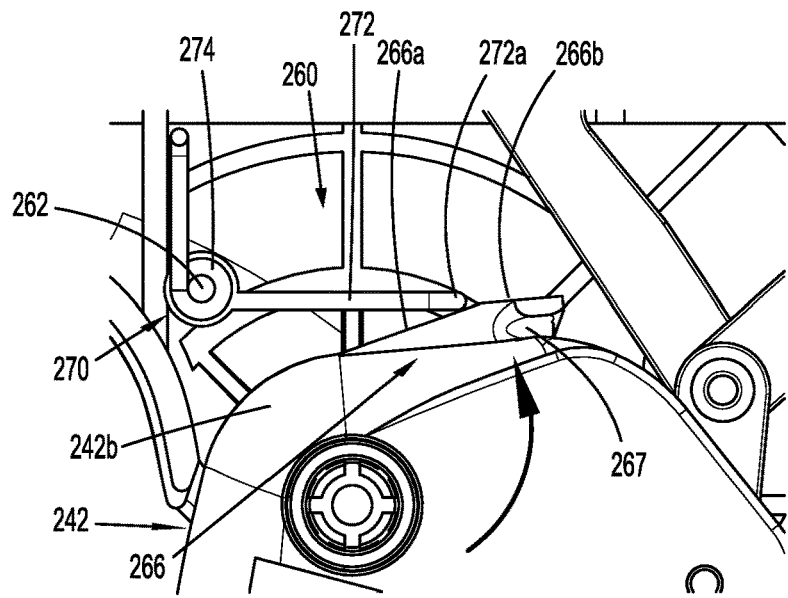
FIG. 13 is an enlarged side view of the feedback mechanism shown in FIG. 11 with a trigger in a partially actuated position.

With particular reference to FIG. 13, upon actuation of the trigger member 242, e.g., proximal pivoting of the grasping portion 242a of the trigger member 242 toward the fixed handle portion 214 of the housing 210, the intermediate pivot portion 242b of the trigger member 242 moves in a counter-clockwise direction, as indicated by arrow "G". The counter-clockwise movement of the intermediate pivot portion 242b of the trigger member 242 causes the hammer portion 272a on the free end of the elongate body 272 of the torsion spring 270 to ride along the inclined surface 266a of the ramp portion 266 of the feedback mechanism 260. During actuation of the trigger member 242, the engagement portion 276a on the free end of the flange portion 276 of the torsion spring 270 remains in a fixed position. The movement of the hammer portion 272a of the torsion spring 270 along the inclined surface 266a of the ramp portion 266 cams the spring portion 274 of the torsion spring 270 to a loaded condition.

Figure 14:
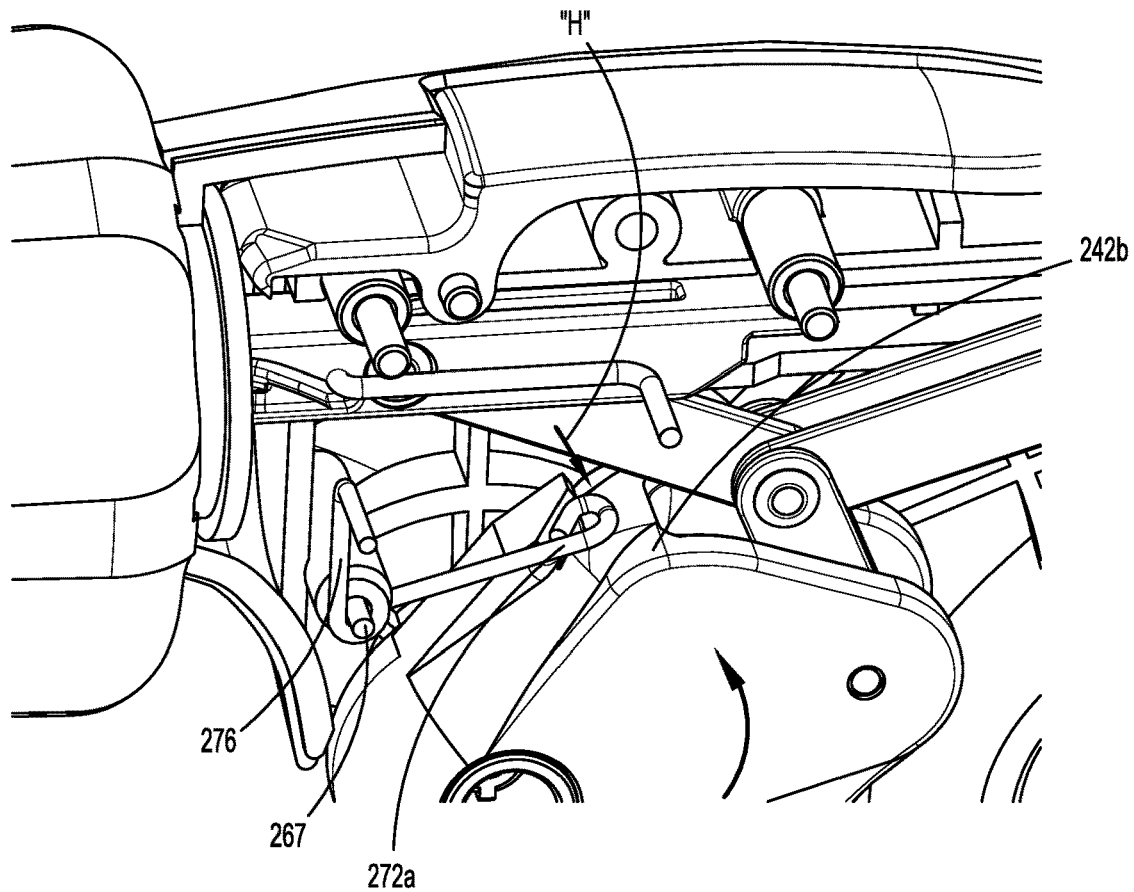
FIG. 14 is a side perspective view of the feedback mechanism shown in FIG. 11 with the trigger in a fully actuated position.

Turning to FIG. 14, the ramp portion 266 and the torsion spring 270 of the feedback mechanism 260 are configured such that at the end of the actuation stroke, the hammer portion 272a of the torsion spring 270 disengages from the edge surface 266b of the ramp portion 266. As noted above, during actuation of the trigger member 242, the spring portion 274 is cammed to the loaded condition. In this manner, when the hammer portion 272a of the torsion spring 270 disengages from the edge surface 266b of the ramp 262, the hammer portion 272a snaps against the outer surface of the intermediate pivot portion 242b of the trigger member 242, as indicated by arrow "H", thereby producing an audible response. It is envisioned that the contact of the hammer portion 272a of the torsion spring 270 may also produce a tactile response, e.g., vibration.

Figure 15:
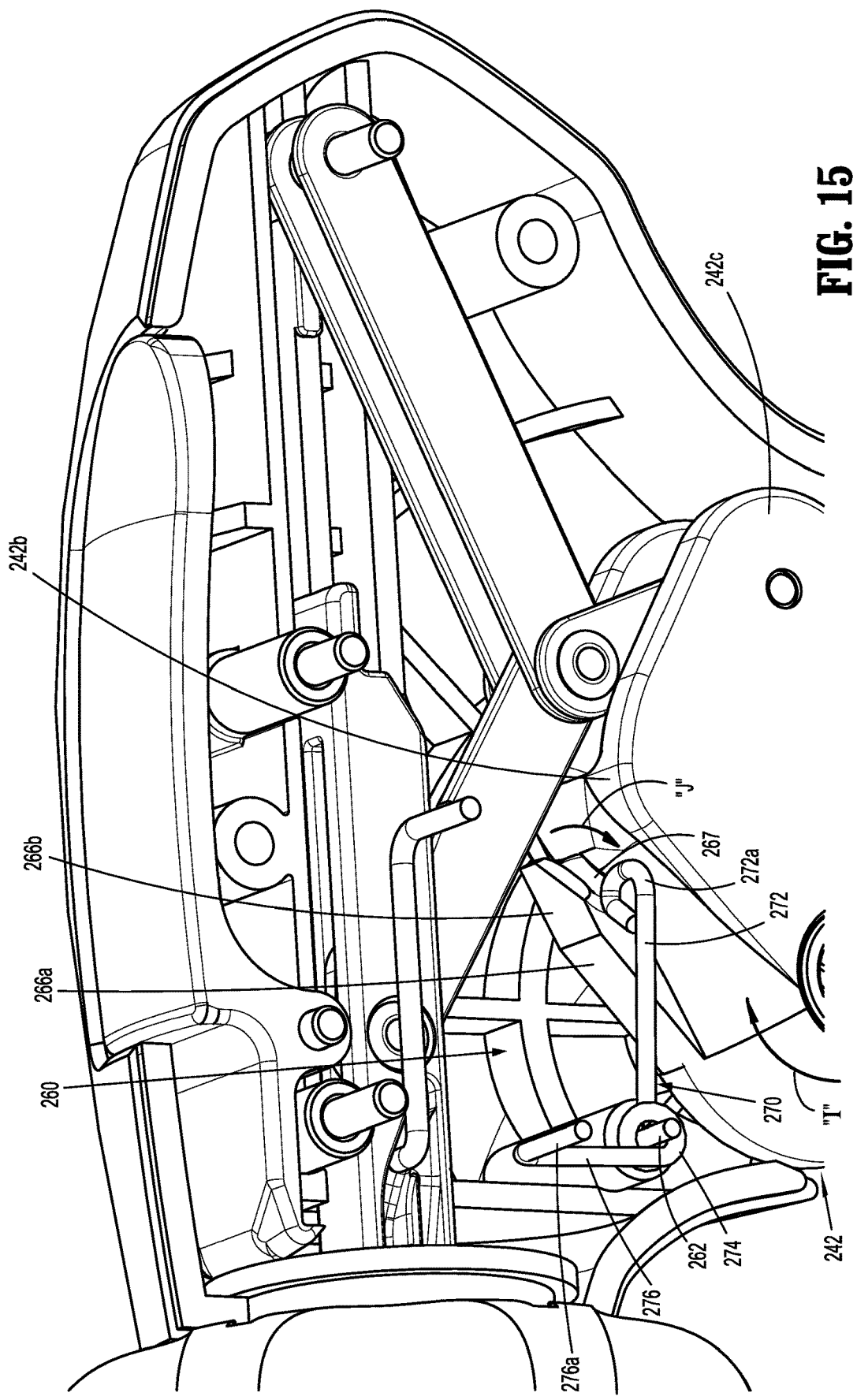
FIG. 15 is an enlarged side perspective view of the feedback mechanism shown in FIG. 11 with the trigger in a partially returned position.
Figure 16:
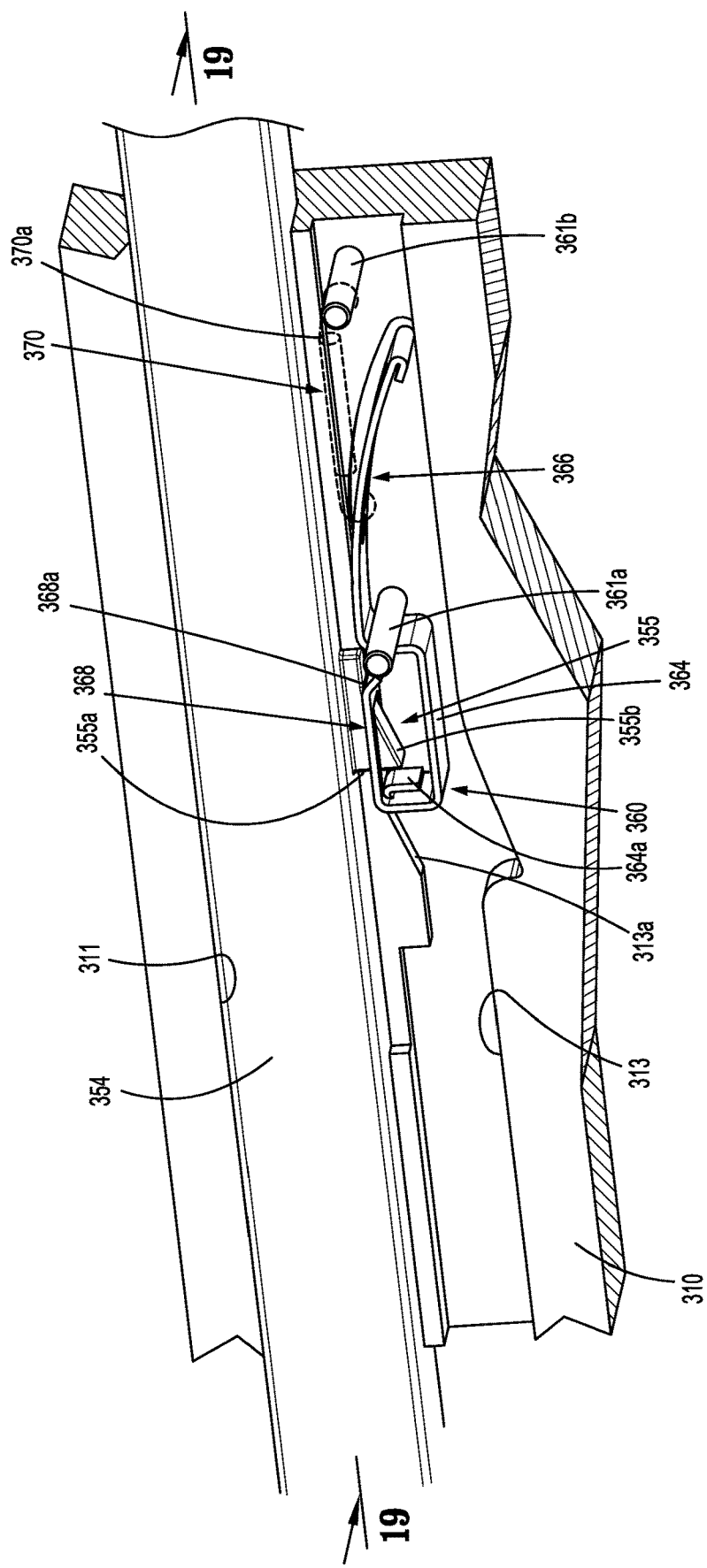
FIG. 16 is a side perspective view of a feedback mechanism according to another embodiment of the present disclosure.

With reference to FIG. 15, as the trigger member 242 returns to its initial position, as indicated by arrow "I", the elongate body 272 of the torsion spring 270 advances relative to the ramp portion 266 such that the hammer portion 272a of the torsion spring 270 engages the cam track 267 of the ramp portion 266. As the hammer portion 272a engages the cam track 267 of the ramp portion 266, the hammer portion 272a is guided around the ramp portion 266, as indicated by arrow "J", to return to its initial position disposed along the inclined surface 266a of the ramp portion 266, thereby resetting the feedback mechanism 260, and readying the handle assembly 200 for further use.

With reference now to FIGS. 16-22, a feedback mechanism according to another embodiment of the present disclosure is shown generally as feedback mechanism 360. The feedback mechanism 360 is slidably supported within a longitudinal channel 311 of a housing 310 of a handle assembly (not shown) relative to a drive bar 354. The drive bar 354 is substantially similar in structure and operation to the drive bars 154, 254 of the respective handle assembly 100, 200 described hereinabove, advancing from an initial position during a firing stroke and retracting to the initial position following the firing stroke.

The feedback mechanism 360 includes a hammer member 362 and a tension spring 370. The hammer member 362 is slidably supported within a longitudinal cutout 313 of the housing 310 between a first pin 361a disposed within the housing 310 and the drive bar 354. A first end 370a of the tension spring 370 is secured to a second pin 361b disposed within the housing 310 and a second end 370b of the tension spring 370 is secured to the hammer member 362. As will be described below, the feedback mechanism 360 is configured such that advancement of the drive bar 354 during a firing stroke causes simultaneous advancement of the hammer member 362. A ramped portion 313a of the housing 310 extends within the longitudinal cutout 313 and is configured to deflect the C-shaped body portion 364 of the hammer member 362 away from a ramp portion 355 of the drive bar 354 as the drive bar 354 and the hammer member 362 are advanced.

Figure 17:
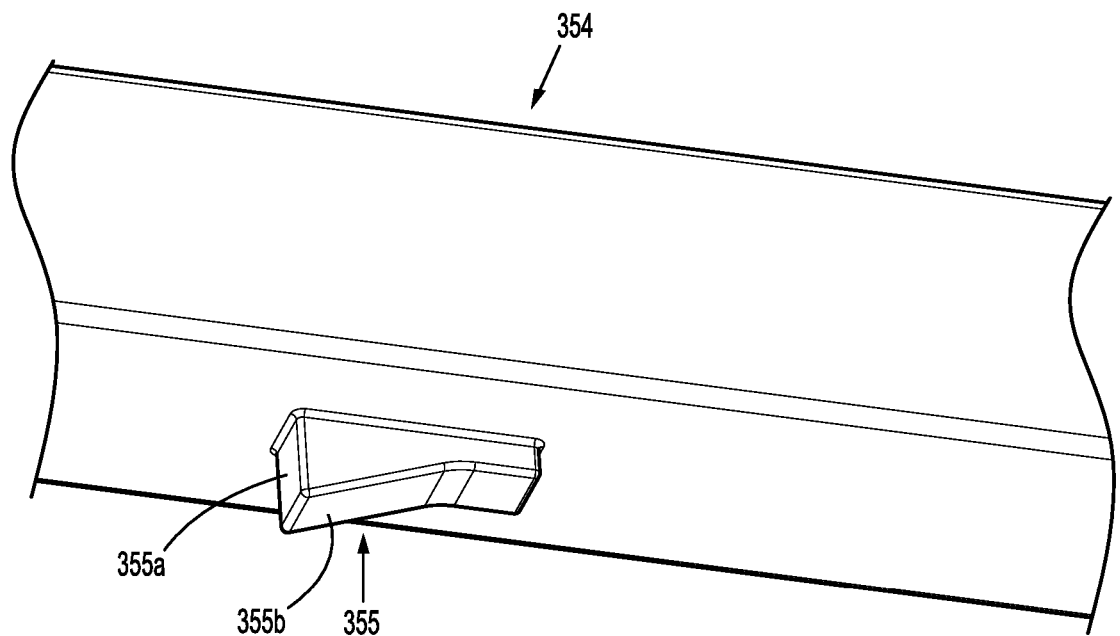
FIG. 17 is a side perspective view of a hammer member of the feedback mechanism shown in FIG. 16.

With particular reference to FIG. 17, the ramp portion 355 of the drive bar 354 includes a contact surface 355a and an inclined surface 355b. The contact surface 355a of the ramp portion 355 engages the hammer member 362 during a firing stroke to cause distal movement of the hammer member 362 along with the drive bar 354. The inclined surface 355b of the ramp portion 355 facilitates resetting of the hammer member 362 subsequent to the completion of the firing stroke.

Figure 18:
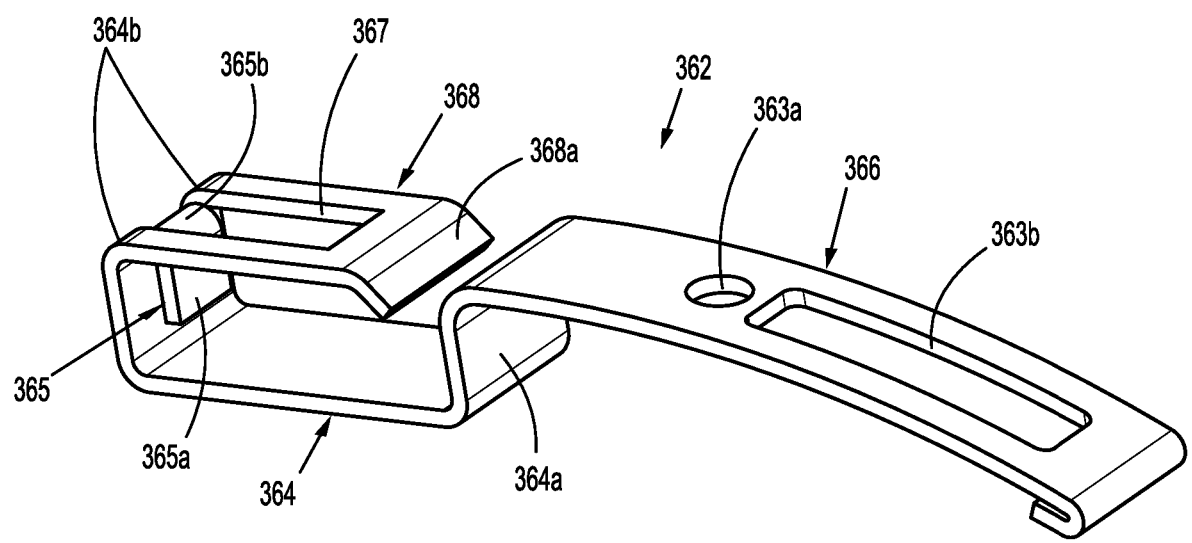
FIG. 18 is an enlarged side perspective view of a ramp of the feedback mechanism shown in FIG. 16 extending from a drive bar.

Referring to FIG. 18, the hammer member 362 of the feedback mechanism 360 includes a C-shaped body portion 364, a proximal spring attachment portion 366 extending from a first side of the C-shaped body portion 364, and a flange portion 368 extending from a second side of the C-shaped body portion 364. The C-shaped body portion 364 includes a pin engagement surface 364a configured to engage the first pin 361a in the housing 310 to create an audible and/or tactile response upon completion of the firing stroke and a return of the hammer member 362 to its initial position. The proximal spring attachment portion 366 of the hammer member 362 defines an aperture 363a and a slot 363b. The apertures 363a and the slot 363b facilitate engagement of the tension spring 370 with the hammer member 362. The flange portion 368 of the hammer member 362 extends proximally towards the proximal spring attachment portion 366 and includes a bent free end 368a.

With continued reference to FIG. 18, the flange portion 368 of the hammer member 362 defines an opening 367 through which the ramp portion 355 extending from the drive bar 354 is received. A tab portion 365 extends from the C-shaped body portion 364 of the hammer member 362 adjacent the opening 367 in the flange portion 368. A proximal facing surface 365a of the tab portion 365 engages the contact surface 355a of the ramp portion 355 during a firing stroke. Top surfaces 364b of the C-shaped body portion 364 are configured to engage the ramped portions 313a of the housing 310 as the hammer member 362 is advanced by the drive bar 354 through longitudinal cutout 313 of housing 310 to deflect the C-shaped body portion 364 away from the ramp portion 355 to cause the hammer member 362 to disengage from the ramp portion 355.

Figure 19:
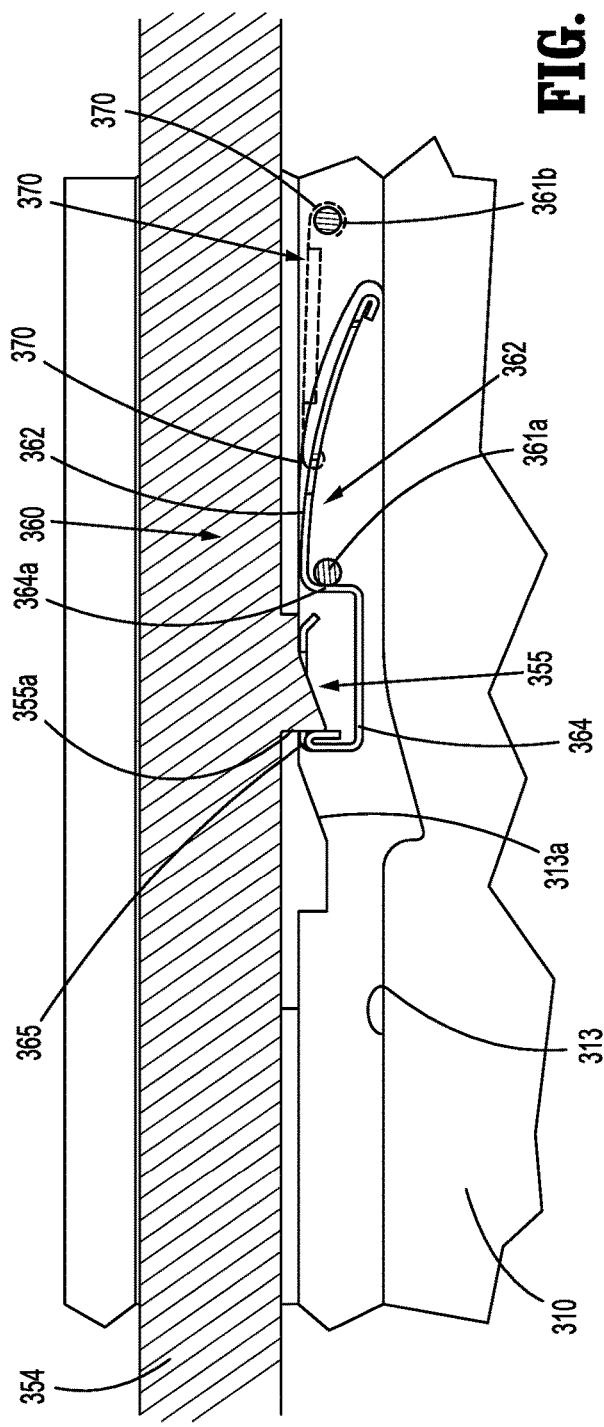
FIG. 19 is a cross-sectional side view taken along line 19-19 shown in FIG. 16, with the drive bar in a first or fully retracted position.

Turning to FIG. 19, when the handle assembly (not shown) is in an initial or pre-actuated condition, the contact surface 355a of the ramp portion 355 of the drive bar 354 engages the proximal facing surface 365a of the tab portion 365 of the C-shaped body portion 364 of the hammer member 362, and the pin engagement surface 364a of the C-shaped body portion 364 engages the first pin 361a. As the drive bar 354 is advanced, as indicated by arrow "K" shown in FIG. 20, the hammer member 362 is also advanced.

Figure 20:
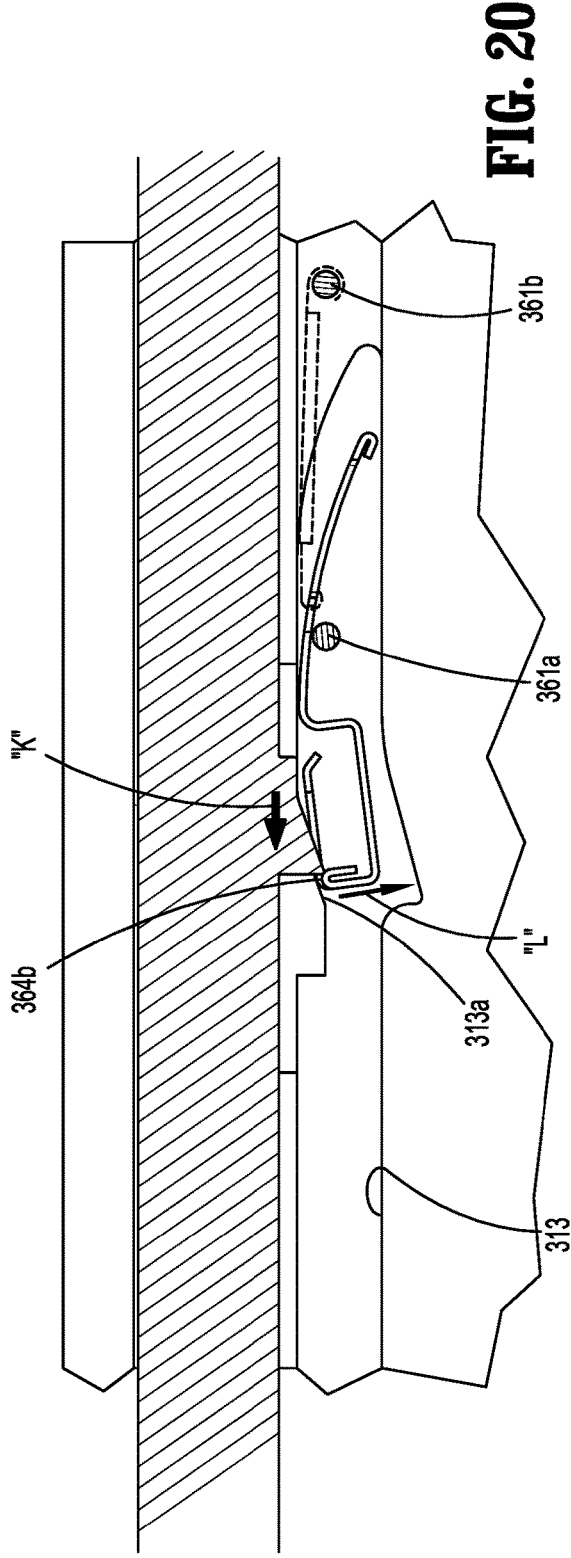
FIG. 20 is a cross-sectional side view taken along line 19-19 shown in FIG. 16, with the drive bar in a partially advanced position.
Figure 24:
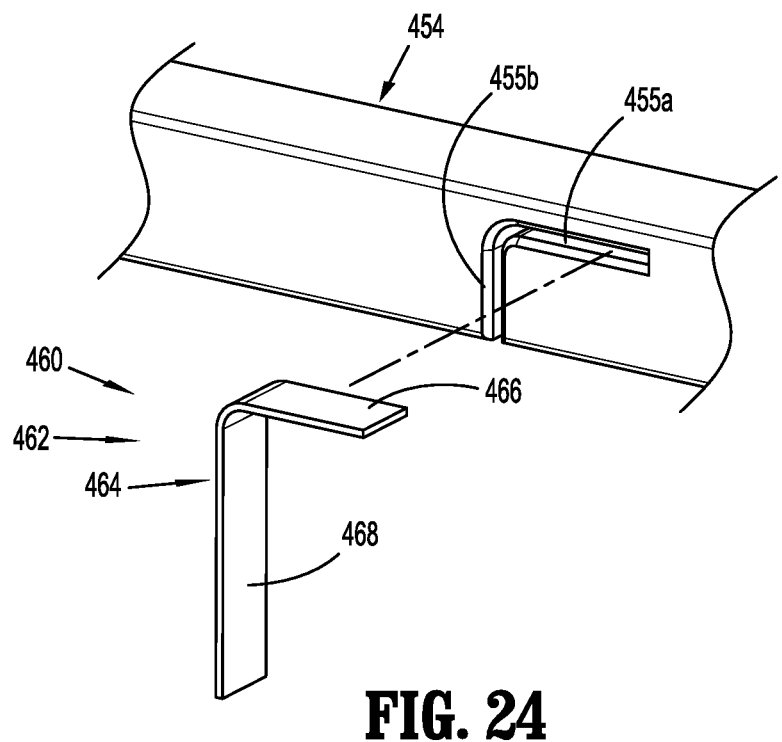
FIG. 24 is a perspective view of a spring member of the feedback mechanism shown in FIG. 23.

Turning to FIG. 20, as noted above, as the drive bar 354 is advanced, the hammer member 362 is simultaneously advanced. As the hammer member 362 is advanced, the top surfaces 364b of the C-shaped body portion 364 engage the ramped portions 313a of the housing 310. Continued advancement of the hammer member 362 relative to the ramped portions 313a of the housing 310 causes the C-shaped body portion 364 of the hammer member 362 to deflect away from the ramp portion 355 of the drive member 354, as indicated by arrow "L", to cause the hammer member 362 to disengage from the ramp portion 355 of the drive member 354 upon completion of the firing stroke. Advancement of the hammer member 362 also cause the tension spring 370 to stretch to a loaded condition.

With reference to FIG. 21, when the hammer member 362 disengages from the ramped portion 313a of the housing 310, the hammer member 362 snaps back to its initial position, as indicated by arrow "M", as the tension spring 270 returns to its initial or unloaded condition. As the hammer member 362 snaps back to its initial position, the contact portion 364a of the C-shaped body portion 364 engages the first pin 361 creating an audible response. As noted above, it is envisioned that the engagement of the hammer member 362 with the first pin 361 may also produce a tactile response, e.g., vibration.

Turning to FIG. 22, following the completion of the actuation stroke, the drive bar 354 retracts to its initial position to reset and prepare the handle assembly (not shown) for a subsequent firing. As the drive bar 354 retracts relative to the hammer member 362, as indicated by arrow "N", the top surface 365b of the tab portion 365 of the hammer member 362 engages the inclined surface 355b of the ramp portion 355 of the drive bar 354. As the ramp portion 355 engages the hammer member 362, the C-shaped body portion 364 of the hammer member 362 is guided over the ramp portion 355 to facilitate resetting of the feedback mechanism 360.

With reference now to FIGS. 23-27, another embodiment of a feedback mechanism according to the present disclosure is shown generally as feedback mechanism 460. With initial reference to FIGS. 23 and 24, the feedback mechanism 460 includes a spring member 462 secured to a drive bar 454 supported with a housing 410 of a handle assembly (not shown). The flexible member 462 includes a substantially L-shaped body 464 having an anchor portion 466 and an engagement portion 468. The anchor portion 466 of the flexible member 462 is received in a longitudinal slot 455a in the drive bar 454 and the engagement portion 468 is received in and extends from a transverse slot 455b in the drive bar 454.

Figure 25:
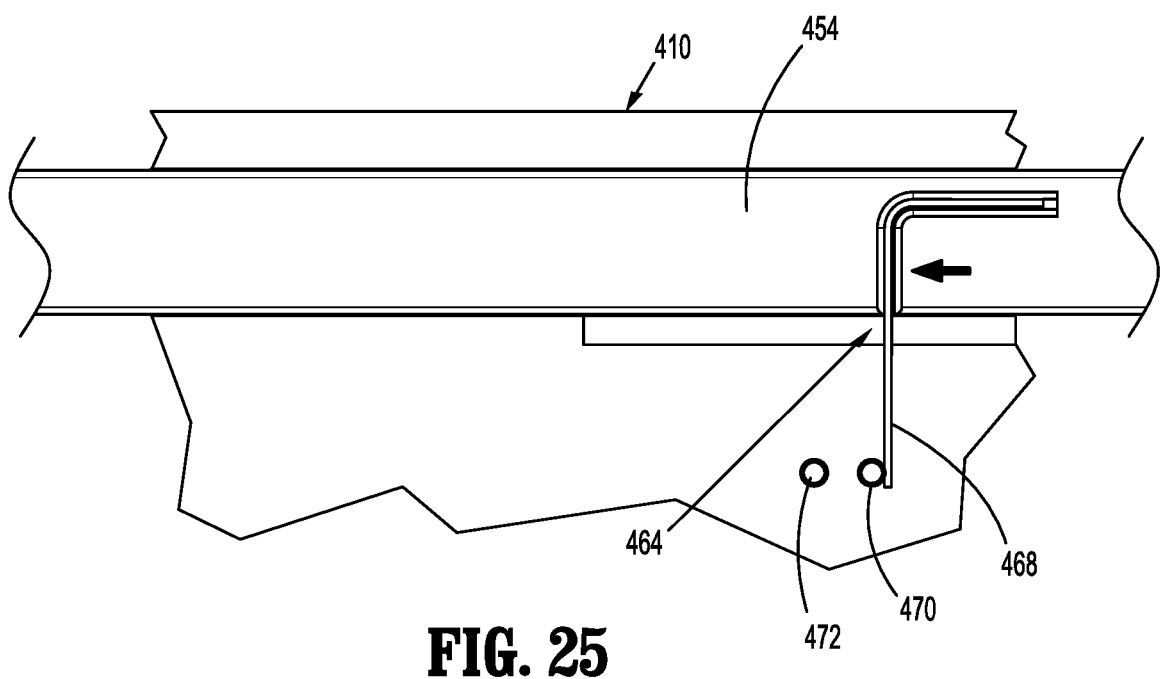
FIG. 25 is a side view of the feedback mechanism shown in FIG. 23 with a drive bar in a first or fully retracted position.

With reference to FIG. 25, the engagement portion 468 of the flexible member 262 of the feedback mechanism 460 is positioned to engage a first pin 470 disposed within the housing 410 during advancement of the drive bar 454, e.g., as the handle assembly (not shown) is actuated.

Figure 26:
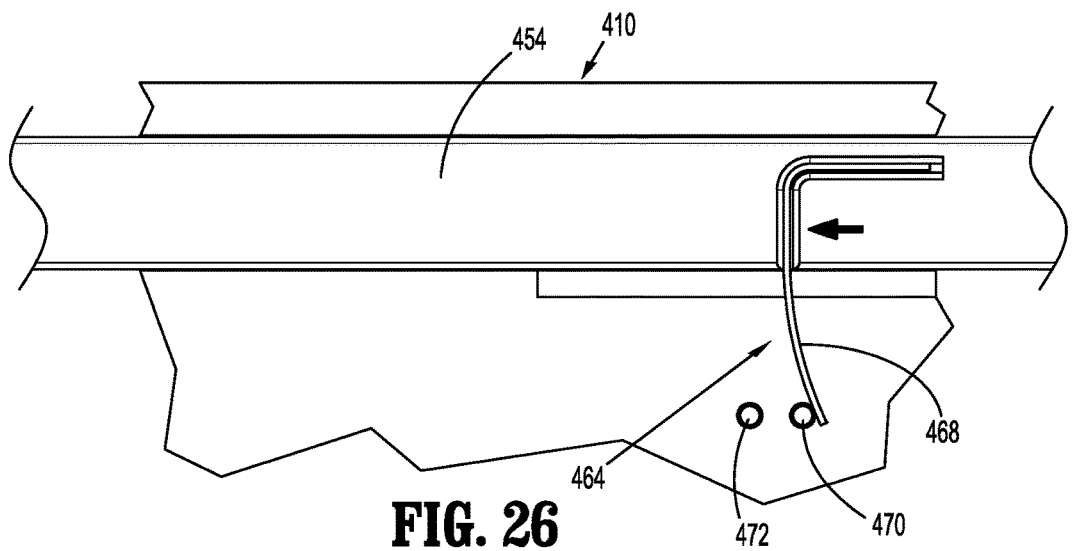
FIG. 26 is a side view of the feedback mechanism shown in FIG. 23 with the drive bar in a partially advanced position.

Turning to FIG. 26, continued advancement of the drive bar 454 causes the engagement portion 468 of the flexible member 462 to flex, e.g., transition to a loaded condition.

Figure 27:
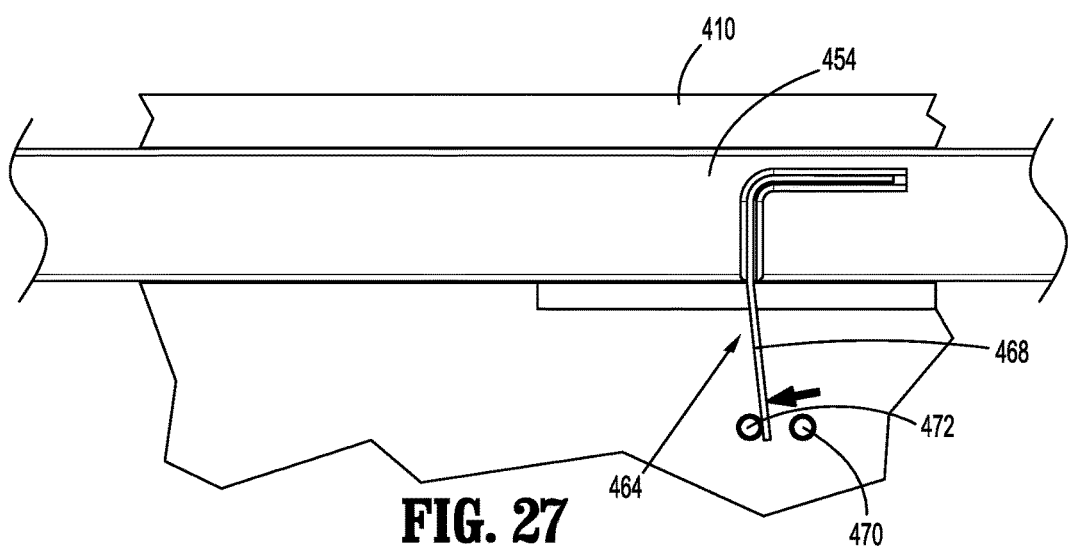
FIG. 27 is a side view of the feedback mechanism shown in FIG. 23 with the drive bar in a fully advanced position.

With reference to FIG. 27, the flexible member 462 is position such that at the completion of the firing stroke, the drive bar 454 has advanced sufficiently enough to cause the engagement portion 468 of the flexible member 462 to disengage from the first pin 470. The snapping action of the engagement portion 468 of the flexible member 462 caused by the unflexing or straightening of the flexed flexible member 462 results in the engagement portion 468 striking a second pin 472 disposed within the housing 410. The striking of the flexible member 462 against the second pin 472 causes an audible response.

Return of the drive bar 454 to its original position resets the feedback mechanism 460.

Figure 28:
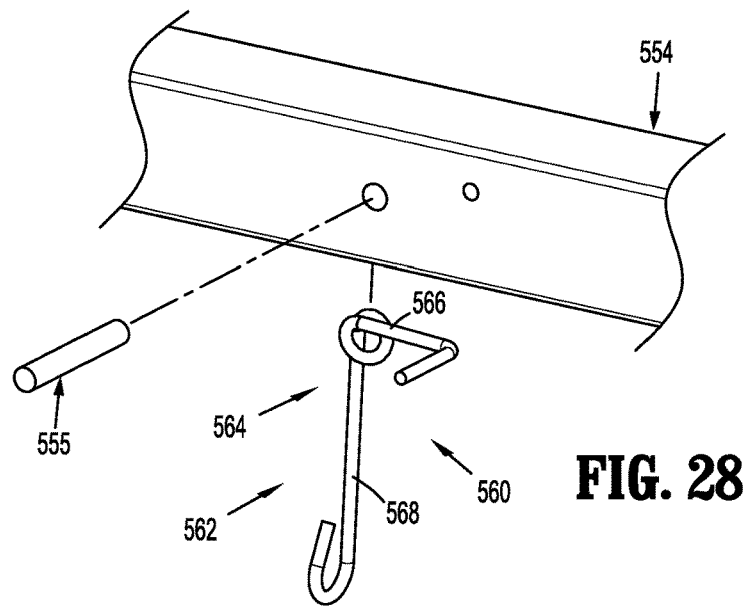
FIG. 28 is a perspective view of a feedback mechanism according to still another embodiment of the present disclosure.

Turning to FIG. 28, a feedback mechanism according another embodiment of the present disclosure is shown generally as feedback mechanism 560. The feedback mechanism 560 is substantially similar to the feedback mechanism 460 described above. The feedback mechanism 560 includes a flexible member 562 in the form of a torsion spring 564 supported on a drive bar 554 by pivot member 555. The torsion spring 564 includes a spring portion 566 and an engagement portion 568.

Similar to the flexible member 462 described above, advancement of the drive bar 554 during a firing stroke of the handle assembly (not shown) causes the engagement portion 568 of the torsion spring 564 to engage a first pin 470 (FIG. 25). Continued advancement of the drive bar 554 causes the engagement portion 568 of the torsion spring 564 to flex. Upon completion of the firing stroke, e.g., distal most advancement of the drive bar 554, the engagement portion 568 of the torsion spring 564 disengages from the first pin 470 and strikes against the second pin 472 (FIG. 27) causing an audible and/or tactile response. Return of the drive bar 554 to its initial position resets the feedback mechanism 460.

It should be understood that the foregoing description is only illustrative of the present disclosure. Various alternatives and modifications can be devised by those skilled in the art without departing from the disclosure. Accordingly, the present disclosure is intended to embrace all such alternatives, modifications and variances. The embodiments described with reference to the attached drawing figures are presented only to demonstrate certain examples of the disclosure. Other elements, steps, methods and techniques that are insubstantially different from those described above and/or in the appended claims are also intended to be within the scope of the disclosure.

What is claimed is:

1. A handle assembly, comprising:
    a housing including a body portion defining a longitudinal axis and a stationary handle extending from the body portion;
    a trigger operably coupled to the housing and movable towards the stationary handle to cause actuation of the handle assembly;
    a drive member movable within the housing from an initial position to an advanced position in response to actuation of the trigger; and
    a feedback mechanism in operable engagement with the trigger, the feedback mechanism including a torsion spring having a hammer portion, wherein upon complete actuation of the handle assembly the hammer portion of the torsion spring strikes a surface to create at least one of an audible or a tactile response.

2. The handle assembly of claim 1, wherein the housing includes a body portion and a trigger portion.

3. The handle assembly of claim 2, wherein the feedback mechanism includes a ramp portion.

4. The handle assembly of claim 3, wherein the hammer portion of the torsion spring engages the ramp portion during actuation of the handle assembly to transition the torsion spring to a loaded condition.

5. The handle assembly of claim 4, wherein upon complete actuation of the handle assembly, the hammer portion of the torsion spring disengages the ramp portion to unload the torsion spring.

6. The handle assembly of claim 5, wherein upon unloading of the torsion spring, the hammer portion strikes the surface to create the at least one audible or tactile response.

7. The handle assembly of claim 1, wherein a first end of the torsion spring is secured relative to the trigger.

8. The handle assembly of claim 7, wherein the torsion spring includes a spring portion, the spring portion being received about a pivot pin secured to the trigger.

9. The handle assembly of claim 1, wherein the torsion spring is moved to a loaded condition during actuation of the handle assembly.

10. A handle assembly, comprising:
    a housing defining a longitudinal axis;
    a trigger operably coupled to the housing and movable to cause actuation of the handle assembly;
    a drive member supported within the housing and movable in response to actuation of the trigger; and
    a feedback mechanism in operable engagement with the trigger, the feedback mechanism including a spring member pivotally supported on the trigger and having a striking portion, wherein upon complete actuation of the handle assembly the striking portion of the spring member strikes a surface to create at least one of an audible or a tactile response.

11. The handle assembly of claim 10, wherein the housing includes a body portion and a trigger portion.

12. The handle assembly of claim 11, wherein the feedback mechanism includes a ramp portion.

13. The handle assembly of claim 12, wherein the striking portion of the spring member engages the ramp portion during actuation of the handle assembly to transition the spring member to a loaded condition.

14. The handle assembly of claim 13, wherein upon complete actuation of the handle assembly, the striking portion of the spring member disengages the ramp portion to unload the spring member.

15. The handle assembly of claim 14, wherein upon unloading of the spring member, the striking portion strikes the surface to create the at least one audible or tactile response.

16. The handle assembly of claim 10, wherein a first end of the spring member is secured relative to the trigger.

17. The handle assembly of claim 16, wherein the spring member includes a spring portion, the spring portion being received about a pivot pin secured to the trigger.

18. The handle assembly of claim 10, wherein the spring member is moved to a loaded condition during actuation of the handle assembly.

19. A handle assembly, comprising:
a housing;
a trigger operably coupled to the housing and movable to cause actuation of the handle assembly;
a drive member movable within the housing from an initial position to an advanced position in response to actuation of the trigger; and
a feedback mechanism in operable engagement with the trigger, the feedback mechanism including a torsion spring pivotally supported on the trigger and having a hammer portion, wherein upon complete actuation of the handle assembly the hammer portion of the torsion spring strikes a surface to create at least one of an audible or a tactile response.

20. The handle assembly of claim 19, wherein the housing includes a body portion and a trigger portion.

* * * * *